(12) United States Patent
Pinter et al.

(10) Patent No.: US 9,098,611 B2
(45) Date of Patent: Aug. 4, 2015

(54) ENHANCED VIDEO INTERACTION FOR A USER INTERFACE OF A TELEPRESENCE NETWORK

(71) Applicant: INTOUCH HEALTH, Goleta, CA (US)

(72) Inventors: Marco Pinter, Santa Barbara, CA (US); Charles S. Jordan, Santa Barbara, CA (US); Daniel Sanchez, Summerland, CA (US); Kevin Hanrahan, Santa Barbara, CA (US); Chris Lambrecht, Santa Barbara, CA (US); Kelton Temby, Goleta, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 23 days.

(21) Appl. No.: 13/830,334

(22) Filed: Mar. 14, 2013

(65) Prior Publication Data

US 2014/0267549 A1     Sep. 18, 2014

Related U.S. Application Data

(60) Provisional application No. 61/729,964, filed on Nov. 26, 2012.

(51) Int. Cl.
| | |
|---|---|
| H04N 7/14 | (2006.01) |
| G06F 19/00 | (2011.01) |
| H04N 7/18 | (2006.01) |

(52) U.S. Cl.
CPC ............ *G06F 19/3418* (2013.01); *H04N 7/142* (2013.01); *H04N 7/147* (2013.01); *H04N 7/185* (2013.01)

(58) Field of Classification Search
CPC ...................................... H04N 7/148
USPC ............... 342/44; 345/629; 348/14.08, 14.12, 348/211.8, 684, 14.01, 14.02, 14.03, 584; 370/352; 379/88.13; 382/154; 386/289; 600/474; 701/9, 400, 431; 709/203, 709/204, 231; 715/802; 725/28
See application file for complete search history.

(56) References Cited

U.S. PATENT DOCUMENTS

| | | | |
|---|---|---|---|
| 3,821,995 | A | 7/1974 | Aghnides |
| 4,107,689 | A | 8/1978 | Jellinek |

(Continued)

FOREIGN PATENT DOCUMENTS

| | | |
|---|---|---|
| AU | 2000/012162 A | 10/1999 |
| CA | 2289697 A1 | 11/1998 |

(Continued)

OTHER PUBLICATIONS

"Appeal from the U.S. District Court for the Central District of California in No. 11-CV-9185, Judge Percy Anderson", May 9, 2014, pp. 1-48.

(Continued)

*Primary Examiner* — Gerald Gauthier

(57) ABSTRACT

A telepresence device may relay video, audio, and/or measurement data to a user operating a control device. A user interface may permit the user to quickly view and/or understand temporally and/or spatially disparate information. The telepresence device may pre-gather looped video of spatially disparate areas in an environment. A temporal control mechanism may start video playback at a desired point in a current or historical video segment. Notations may be associated with time spans in a video and recalled by capturing an image similar to a frame in the time span of the video. An area of interest may be selected and video containing the area of interest may be automatically found. Situational data may be recorded and used to recall video segments of interest. The telepresence device may synchronize video playback and movement. A series of videos may be recorded at predetermined time intervals to capture visually trending information.

33 Claims, 18 Drawing Sheets

(56) References Cited

U.S. PATENT DOCUMENTS

| | | |
|---|---|---|
| 4,213,182 A | 7/1980 | Eichelberger et al. |
| 4,413,693 A | 11/1983 | Derby |
| 4,471,354 A | 9/1984 | Smith |
| 4,519,466 A | 5/1985 | Shiraishi |
| 4,553,309 A | 11/1985 | Hess et al. |
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | George et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane, III et al. |
| 5,006,988 A | 4/1991 | Borenstein et al. |
| 5,040,116 A | 8/1991 | Evans, Jr. et al. |
| 5,051,906 A | 9/1991 | Evans et al. |
| 5,073,749 A | 12/1991 | Kanayama |
| 5,084,828 A | 1/1992 | Kaufman |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen, III et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey |
| 5,374,879 A | 12/1994 | Pin |
| 5,375,195 A | 12/1994 | Johnston |
| 5,400,068 A | 3/1995 | Ishida et al. |
| 5,413,693 A | 5/1995 | Redepenning |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David |
| 5,442,728 A | 8/1995 | Kaufman et al. |
| 5,462,051 A | 10/1995 | Oka |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Collens |
| 5,793,365 A | 8/1998 | Tang et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | DeVault et al. |
| 5,867,494 A | 2/1999 | Krishnaswamy et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober et al. |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |

(56) References Cited

U.S. PATENT DOCUMENTS

| | | |
|---|---|---|
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,304,050 B1 | 10/2001 | Skaar et al. |
| 6,314,631 B1 | 11/2001 | Pryor |
| 6,317,652 B1 | 11/2001 | Osada |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,430,471 B1 | 8/2002 | Kintou et al. |
| 6,430,475 B2 | 8/2002 | Okamoto |
| 6,438,457 B1 | 8/2002 | Yokoo |
| 6,445,964 B1 | 9/2002 | White et al. |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 * | 5/2003 | Granot et al. ............ 342/44 |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,684,129 B2 | 1/2004 | Salisbury et al. |
| 6,691,000 B2 | 2/2004 | Nagai et al. |
| 6,693,585 B1 | 2/2004 | MacLeod |
| 6,710,797 B1 | 3/2004 | McNelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi et al. |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling et al. |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |

(56) References Cited

U.S. PATENT DOCUMENTS

| | | | |
|---|---|---|---|
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 | 5/2007 | Wang et al. |
| 7,227,334 B2 | 6/2007 | Yang et al. |
| 7,256,708 B2 | 8/2007 | Rosenfeld |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 * | 11/2007 | Kang et al. ............... 345/629 |
| 7,292,912 B2 | 11/2007 | Wang et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 * | 4/2008 | Chen et al. ............... 701/9 |
| 7,382,399 B1 | 6/2008 | McCall |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'Rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | DiRienzo |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 * | 4/2010 | Dawson ............... 725/28 |
| 7,719,229 B2 | 5/2010 | Kaneko et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,774,158 B2 | 8/2010 | Domingues et al. |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,885,822 B2 | 2/2011 | Akers et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,763 B2 | 7/2011 | King |
| 7,982,769 B2 | 7/2011 | Jenkins et al. |
| 7,987,069 B2 | 7/2011 | Rodgers et al. |
| 8,077,963 B2 | 12/2011 | Wang et al. |
| 8,116,910 B2 | 2/2012 | Walters et al. |
| 8,126,960 B2 * | 2/2012 | Obradovich et al. ......... 709/203 |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Wang et al. |
| 8,212,533 B2 | 7/2012 | Ota |
| 8,265,793 B2 | 9/2012 | Cross et al. |
| 8,287,522 B2 | 10/2012 | Moses et al. |
| 8,292,807 B2 | 10/2012 | Perkins et al. |
| 8,320,534 B2 * | 11/2012 | Kim et al. ............... 379/88.13 |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,374,171 B2 * | 2/2013 | Cho et al. ............... 370/352 |
| 8,400,491 B1 | 3/2013 | Panpaliya et al. |
| 8,401,275 B2 | 3/2013 | Wang et al. |
| 8,423,284 B2 * | 4/2013 | O'Shea ............... 701/400 |
| 8,451,731 B1 | 5/2013 | Lee et al. |
| 8,463,435 B2 | 6/2013 | Herzog et al. |
| 8,503,340 B1 | 8/2013 | Xu |
| 8,515,577 B2 | 8/2013 | Wang et al. |
| 8,527,094 B2 | 9/2013 | Kumar et al. |
| 8,531,502 B2 * | 9/2013 | Cheng et al. ............... 348/14.08 |
| 8,532,860 B2 | 9/2013 | Daly |
| 8,610,786 B2 * | 12/2013 | Ortiz ............... 348/211.8 |
| 8,639,797 B1 | 1/2014 | Pan et al. |
| 8,670,017 B2 | 3/2014 | Stuart et al. |
| 8,726,454 B2 | 5/2014 | Gilbert et al. |
| 8,836,751 B2 | 9/2014 | Ballantyne et al. |
| 8,849,679 B2 | 9/2014 | Wang et al. |
| 8,849,680 B2 | 9/2014 | Wright et al. |
| 8,861,750 B2 | 10/2014 | Roe et al. |
| 8,897,920 B2 | 11/2014 | Wang et al. |
| 8,902,278 B2 | 12/2014 | Pinter et al. |
| 2001/0002448 A1 | 5/2001 | Wilson |
| 2001/0010053 A1 | 7/2001 | Ben-Shachar et al. |
| 2001/0020200 A1 | 9/2001 | Das et al. |
| 2001/0034475 A1 | 10/2001 | Flach et al. |
| 2001/0034544 A1 | 10/2001 | Mo |
| 2001/0037163 A1 | 11/2001 | Allard |
| 2001/0048464 A1 | 12/2001 | Barnett |
| 2001/0051881 A1 | 12/2001 | Filler |
| 2001/0054071 A1 | 12/2001 | Loeb |
| 2001/0055373 A1 | 12/2001 | Yamashita |
| 2002/0015296 A1 | 2/2002 | Howell et al. |
| 2002/0027597 A1 | 3/2002 | Sachau |
| 2002/0027652 A1 | 3/2002 | Paromtchik et al. |
| 2002/0033880 A1 | 3/2002 | Sul et al. |
| 2002/0038168 A1 | 3/2002 | Kasuga et al. |
| 2002/0044201 A1 | 4/2002 | Alexander et al. |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0085030 A1 | 7/2002 | Ghani |
| 2002/0095238 A1 | 7/2002 | Ahlin et al. |
| 2002/0095239 A1 | 7/2002 | Wallach et al. |
| 2002/0098879 A1 | 7/2002 | Rheey |
| 2002/0104094 A1 | 8/2002 | Alexander et al. |
| 2002/0106998 A1 | 8/2002 | Presley et al. |
| 2002/0109770 A1 | 8/2002 | Terada |
| 2002/0109775 A1 | 8/2002 | White et al. |
| 2002/0111988 A1 | 8/2002 | Sato |
| 2002/0120362 A1 | 8/2002 | Lathan et al. |
| 2002/0128985 A1 | 9/2002 | Greenwald |
| 2002/0130950 A1 | 9/2002 | James et al. |
| 2002/0133062 A1 | 9/2002 | Arling et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183894 A1 | 12/2002 | Wang |

(56) References Cited

U.S. PATENT DOCUMENTS

| | | |
|---|---|---|
| 2002/0184674 A1 | 12/2002 | Xi et al. |
| 2002/0186243 A1 | 12/2002 | Ellis et al. |
| 2003/0021107 A1 | 1/2003 | Howell et al. |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114962 A1 | 6/2003 | Niemeyer et al. |
| 2003/0120714 A1 | 6/2003 | Wolff et al. |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0195662 A1 | 10/2003 | Wang et al. |
| 2003/0199000 A1 | 10/2003 | Valkirs et al. |
| 2003/0206242 A1 | 11/2003 | Choi et al. |
| 2003/0212472 A1 | 11/2003 | McKee |
| 2003/0216833 A1 | 11/2003 | Mukai et al. |
| 2003/0216834 A1 | 11/2003 | Allard |
| 2003/0220541 A1 | 11/2003 | Salisbury et al. |
| 2003/0220715 A1 | 11/2003 | Kneifel, II et al. |
| 2003/0231244 A1 | 12/2003 | Bonilla et al. |
| 2003/0232649 A1 | 12/2003 | Gizis |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley, Jr. et al. |
| 2004/0010344 A1 | 1/2004 | Hiratsuka |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0240981 A1 | 12/2004 | Dothan et al. |
| 2004/0241981 A1 | 12/2004 | Doris et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick et al. |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0264649 A1* | 12/2005 | Chang et al. ............... 348/14.12 |
| 2005/0267826 A1 | 12/2005 | Levy et al. |
| 2005/0283414 A1 | 12/2005 | Fernandes et al. |
| 2005/0286759 A1* | 12/2005 | Zitnick et al. ................ 382/154 |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |

(56) References Cited

U.S. PATENT DOCUMENTS

| | | |
|---|---|---|
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi et al. |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0064092 A1 | 3/2007 | Sandberg et al. |
| 2007/0078566 A1 | 4/2007 | Wang et al. |
| 2007/0093279 A1 | 4/2007 | Janik |
| 2007/0112700 A1 | 5/2007 | Den et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0182811 A1* | 8/2007 | Rockefeller et al. ....... 348/14.02 |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Ikentani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'Andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0021572 A1* | 1/2009 | Garudadri et al. ......... 348/14.01 |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0237317 A1 | 9/2009 | Rofougaran |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0228249 A1 | 9/2010 | Mohr et al. |
| 2010/0268383 A1 | 10/2010 | Wang et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0153198 A1 | 6/2011 | Kokkas et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |

(56) References Cited

U.S. PATENT DOCUMENTS

| | | |
|---|---|---|
| 2011/0218674 A1 | 9/2011 | Stuart et al. |
| 2011/0245973 A1 | 10/2011 | Wang et al. |
| 2011/0249079 A1* | 10/2011 | Santamaria et al. ........ 348/14.02 |
| 2011/0280551 A1* | 11/2011 | Sammon ..................... 386/289 |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1* | 3/2012 | Wang ........................ 709/231 |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0191246 A1 | 7/2012 | Roe |
| 2012/0191464 A1 | 7/2012 | Stuart et al. |
| 2012/0203731 A1 | 8/2012 | Nelson et al. |
| 2012/0218374 A1* | 8/2012 | Matula et al. .............. 348/14.12 |
| 2012/0291809 A1 | 11/2012 | Kuhe et al. |
| 2013/0250938 A1 | 9/2013 | Anandakumar et al. |
| 2014/0047022 A1* | 2/2014 | Chan et al. ................... 709/204 |
| 2014/0085543 A1* | 3/2014 | Hartley et al. ................ 348/584 |
| 2014/0135990 A1 | 5/2014 | Stuart et al. |
| 2014/0139616 A1* | 5/2014 | Pinter et al. ................ 348/14.08 |
| 2014/0155755 A1* | 6/2014 | Pinter et al. .................... 600/474 |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 92/466492 A2 | 1/1992 |
| EP | 92/488673 A2 | 6/1992 |
| EP | 2002/0981905 A2 | 1/2002 |
| EP | 1232610 B1 | 8/2002 |
| EP | 2002/1262142 A2 | 12/2002 |
| EP | 2003/1304872 A1 | 4/2003 |
| EP | 2004/1536660 A3 | 9/2004 |
| EP | 2005/1536660 A2 | 6/2005 |
| EP | 2005/1573406 A2 | 9/2005 |
| EP | 2005/1594660 A2 | 11/2005 |
| EP | 2007/1763243 A2 | 3/2007 |
| EP | 2007/1791464 A2 | 6/2007 |
| EP | 2007/1800476 A2 | 6/2007 |
| EP | 1819108 A2 | 8/2007 |
| EP | 2007/1856644 A2 | 11/2007 |
| EP | 2008/1928310 A2 | 6/2008 |
| EP | 2009/2027716 A2 | 2/2009 |
| EP | 2010/2145274 A1 | 1/2010 |
| EP | 2010/2214111 A2 | 8/2010 |
| EP | 2010/2263158 A2 | 12/2010 |
| EP | 2011/2300930 A2 | 3/2011 |
| EP | 2011/2342651 A2 | 7/2011 |
| GB | 2431261 A | 4/2007 |
| JP | 07-194609 A | 8/1995 |
| JP | 95/7213753 A | 8/1995 |
| JP | 95/7248823 A | 9/1995 |
| JP | 95/7257422 A | 10/1995 |
| JP | 96/8084328 A | 3/1996 |
| JP | 96/8320727 A | 12/1996 |
| JP | 97/9267276 A | 10/1997 |
| JP | 10079097 | 3/1998 |
| JP | 10288689 A | 10/1998 |
| JP | 11-220706 A | 8/1999 |
| JP | 2000/032319 A | 1/2000 |
| JP | 2000/049800 A | 2/2000 |
| JP | 2000/079587 A | 3/2000 |
| JP | 2000/196876 A | 7/2000 |
| JP | 2001/188124 A | 4/2001 |
| JP | 2001/125641 A | 5/2001 |
| JP | 2001/147718 A | 5/2001 |
| JP | 2001/179663 A | 7/2001 |
| JP | 2001/198865 A | 7/2001 |
| JP | 2001/198868 A | 7/2001 |
| JP | 2001/199356 A | 7/2001 |
| JP | 2002/000574 A | 1/2002 |
| JP | 2002/046088 A | 2/2002 |
| JP | 2002/235423 A | 2/2002 |
| JP | 2002/112970 A | 4/2002 |
| JP | 2002/101333 A | 5/2002 |
| JP | 2002/305743 A | 10/2002 |
| JP | 2002-321180 A | 11/2002 |
| JP | 2002/355779 A | 12/2002 |
| JP | 2004-181229 A | 7/2004 |
| JP | 2004/524824 T | 8/2004 |
| JP | 2004/261941 A | 9/2004 |
| JP | 2004/289379 A | 10/2004 |
| JP | 2005/028066 A | 2/2005 |
| JP | 2005/059170 A | 3/2005 |
| JP | 2005-111083 A | 4/2005 |
| JP | 2006/508806 A | 3/2006 |
| JP | 2006/109094 A | 4/2006 |
| JP | 2006/224294 A | 8/2006 |
| JP | 2006/246438 A | 9/2006 |
| JP | 2007/007040 A | 1/2007 |
| JP | 2007/081646 A | 3/2007 |
| JP | 2007232208 A | 9/2007 |
| JP | 2007316966 A | 12/2007 |
| JP | 2009-125133 A | 6/2009 |
| JP | 2010064154 A | 3/2010 |
| JP | 2010/532109 A | 9/2010 |
| JP | 2010/246954 A | 11/2010 |
| KR | 2006/0037979 A | 5/2006 |
| KR | 2009/0012542 A | 2/2009 |
| KR | 2010/0019479 A | 2/2010 |
| KR | 2010/0139037 A | 12/2010 |
| WO | 93/06690 A1 | 4/1993 |
| WO | 97/42761 A1 | 11/1997 |
| WO | 98/51078 A1 | 11/1998 |
| WO | 99/67067 A2 | 12/1999 |
| WO | 00/25516 A1 | 5/2000 |
| WO | 00/33726 A3 | 6/2000 |
| WO | 01/31861 A1 | 5/2001 |
| WO | 03/077745 A1 | 9/2003 |
| WO | 2004/008738 A1 | 1/2004 |
| WO | 2004/012018 A2 | 2/2004 |
| WO | 2004/075456 A2 | 9/2004 |
| WO | 2006/012797 A1 | 2/2006 |
| WO | 2006/044847 A2 | 4/2006 |
| WO | 2006/078611 A1 | 4/2006 |
| WO | 2007/041295 A1 | 4/2007 |
| WO | 2007/041295 A2 | 4/2007 |
| WO | 2007/041038 A1 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 3/2010 |
| WO | 2010/062798 A1 | 6/2010 |
| WO | 2010/065257 A1 | 6/2010 |
| WO | 2010/120407 A1 | 10/2010 |
| WO | 2011/028589 A2 | 3/2011 |
| WO | 2011/028589 A3 | 4/2011 |
| WO | 2011/097130 A2 | 8/2011 |
| WO | 2011/097132 A2 | 8/2011 |

(56) References Cited

FOREIGN PATENT DOCUMENTS

| | | |
|---|---|---|
| WO | 2011/109336 A2 | 9/2011 |
| WO | 2011/097132 A3 | 12/2011 |
| WO | 2011/149902 A3 | 12/2011 |

OTHER PUBLICATIONS

"Google translation of: Innovations Report", From research project to television star: Care-O-bot in ZDF series, available online at <http://www.innovations-report.de/specials/printa.php?id=5157>, Sep. 28, 2001.
"MPEG File Format Summary", downloaded from: <http://www.fileformat.info/format/mpeg/egff.htm>, Feb. 1, 2001, 8 pages.
"MPEG-4: a Powerful Standard for Use in Web and Television Environments", by Rob Koenen (KPN Research), downloaded from <http://www.w3.org/Architecture/1998/06/Workshop/paper26>, Jul. 1, 1998, 4 pages.
CMU Course 16x62, "Robot user's manual", (describing the Nomad Scout), Carnegie Mellon University, Feb. 1, 2001, 11 pages.
Panusopone et al., "Performance comparison of MPEG-4 and H.263+ for streaming video applications", Circuits Systems Signal Processing, vol. 20, No. 3, 2001, pp. 293-309.
Schraft et al., "Care-O-botTM: The Concept of a System for Assisting Elderly or Disabled Persons in Home Environments", IEEE Proceedings of the 24th Annual Conference of the Industrial Electronics Society, IECON '98, Aug. 31-Sep. 4, 1998, pp. 2476-2481.
Screenshot Showing Google Date for Lemaire Telehealth Manual, Screenshot Retrieved on Dec. 18, 2014, 1 page.
Nomadic Technologies, Inc., "Nomad Scout Language Reference Manual", Software Version: 2.7, Part No. DOC00002, Jul. 12, 1999, 47 pages.
"Appeal from the U.S. District Court for the Central District of California in case No. 11-cv-9185, Judge Percy Anderson, Joint Appendix, vol. I of IV", Jun. 24, 2013, pp. A1-A6357.
"Appeal from the U.S. District Court for the Central District of California in case No. 11-cv-9185, Judge Percy Anderson, Joint Appendix, vol. II of IV", Jun. 24, 2013, pp. A6849-A10634.
"Appeal from the U.S. District Court for the Central District of California in case No. 11-cv-9185, Judge Percy Anderson, Joint Appendix, vol. III of IV", Jun. 24, 2013, pp. A10654-A15517.
"Appeal from the U.S. District Court for the Central District of California in case No. 11-cv-9185, Judge Percy Anderson, Joint Appendix, vol. IV of IV", Jun. 24, 2013, pp. A15677-A18127.
"Reply Brief for Defendant-Appellee VGO Communications, Inc., Appeal from the U.S. District Court for the Central District of California, in Case No. 2:11-cv-9185, Judge Percy Anderson", May 28, 2013, 75 pages.
"Civil Minutes-General: Case No. CV 11-9185PA (AJWx), InTouch Tech., Inc. v. VGO Commons, Inc.", Sep. 10, 2012, 7 pages.
"Opening Brief for Plaintiff-Appellant InTouch Technologies, Inc., Appeal from the U.S. District Court for the Central District of California in Case No. 11-cv-9185, Judge Percy Anderson", Apr. 12, 2013, 187 pages.
"Reply Brief for Plaintiff-Appellant InTouch Technologies, Inc., Appeal from the U.S. District Court for the Central District of California in Case No. 11-cv-9185, Judge Percy Anderson", Jun. 14, 2013, 39 pages.
Office Action received for Chinese Patent Application No. 200680044698.0 on Nov. 4, 2010. (9 pages of Official Copy and 17 pages of English Translation).
"Magne Charge", Smart Power for Electric Vehicles, General Motors Corporation, Serial No. 75189637, Registration No. 2114006, Filing Date: Oct. 29, 1996, Aug. 26, 1997, 2 pages.
"PictureTel Adds New Features and Functionality to its Award-Winning Live200 Desktop Videoconferencing System", PR Newswire Association, LLC, Gale, Cengage Learning, Jun. 13, 1997, 4 pages.
"Using your Infrared Cell Phone Camera", Available on <http://www.catsdomain.com/xray/about.htm>, retrieved on Jan. 23, 2014, Courtesy of Internet Wayback Machine, Jan. 30, 2010, 4 pages.

Activmedia Robotics LLC, "Pioneer 2/PeopleBot™", Operations Manual, Version 9, Oct. 2001, 78 pages.
Adams, Chris, "Simulation of Adaptive Behavior (SAB'02)—From Animals to Animats 7", Mobile Robotics Research Group, The Seventh International Conference, available online at: <http://www.dai.ed.ac.uk/groups/mrg/MRG.html>, retrieved on Jan. 22, 2014, Aug. 4-11, 2002, 1 page.
Evans et al., "HelpMate: The Trackless Robotic Courier", PYXIS, available online at <http://www.pyxis.com/>, 3 pages.
Gaidioz et al., "Synchronizing Network Probes to Avoid Measurement Intrusiveness with the Network Weather Service", High-Performance Distributed Computing, Proceedings of the Ninth International Symposium, 2000, pp. 147-154.
Garner et al., "The Application of Telepresence in Medicine", BT Technology Journal, vol. 15, No. 4, Oct. 1, 1997, pp. 181-187.
Jacobs et al., "Applying Telemedicine to Outpatient Physical Therapy", AMIA, Annual Symposium Proceedings, 2002, 1 page.
Kurlowicz et al., "The Mini Mental State Examination (MMSE)", The Hartford Institute for Geriatric Nursing, Journal of Psychiatric Research, No. 3, Jan. 1999, 2 pages.
Lemaire, Edward, "Using Communication Technology to Enhance Rehabilitation Services", Terry Fox Mobile Clinic, The Rehabilitation Centre, Ottawa, Canada, Version 2.0, 1998-2001, 104 pages.
Nakazato et al., "Group-Based Interface for Content-Based Image Retrieval", Proceedings of the Working Conference on Advanced Visual Interfaces, 2002, pp. 187-194.
Nakazato et al., "Group-Oriented User Interface for Digital Image Management", Journal of Visual Languages and Computing, vol. 14, No. 4, Aug. 2003, pp. 45-46.
North, Michael, "Telemedicine: Sample Script and Specifications for a Demonstration of Simple Medical Diagnosis and Treatment Using Live Two-Way Video on a Computer Network", Greenstar Corporation, 1998, 5 pages.
Piquepaille, Roland, "How New Technologies are Modifying Our Way of Life", Roland Piquepaille's Technology Trends, This Blog and its RSS Feed Are Moving, Oct. 31, 2004, 2 pages.
Radvision, "Making Sense of Bandwidth the NetSense Way", Network Congestion in Unmanaged Networks Bandwidth Estimation and Adaptation Techniques, Radvision's Netsense Technology, 2010, 7 pages.
Telepresence Research, Inc., "Telepresence Mobile Robot System", available online at <http://www.telepresence.com/telepresence-research/TELEROBOT/>, retrieved on Nov. 23, 2010, Feb. 20, 1995, 3 pages.
Theodosiou et al., "MuLVAT: A Video Annotation Tool Based on XML-Dictionaries and Shot Clustering", 19th International Conference, Artificial Neural Networks-ICANN, Sep. 14-17, 2009, pp. 913-922.
Tyrrell et al., "Teleconsultation in Psychology: The Use of Videolinks for Interviewing and Assessing Elderly Patients", British Geriatrics Society, Age and Ageing, vol. 30, No. 3, May 2001, pp. 191-195.
Weaver et al., "Monitoring and Controling Using the Internet and Java", Proceedings of the 25th Annual Conference of the IEEE Industrial Electronics Society, vol. 3, 1999, pp. 1152-1158.
"Nomad Scout User's Manual", Nomadic Technologies, Software Version 2. 7, Part No. DOC00004, Jul. 12, 1999, pp. 1-59.
ACM Digital Library Record, "Autonomous Robots vol. 11 Issue 1", downloaded from <http://dl.acm.org/citation.cfm?id=591550&picked=prox&cfid=360891374&cftoken=35225929>, Jul. 2001, 2 pages.
Brenner, "A technical tutorial on the IEEE 802.11 protocol", BreezeCOM Wireless Communications, 1997, pp. 1-24.
Library of Congress, "008—Fixed-Length Data Elements (NR)", MARC 21 Format for Classification Data, downloaded from http://www.loc.gov/marc/classification/cd008.html, Jan. 2000, pp. 1-14.
Paulos, et al., "Personal Tele-Embodiment", Chapter 9 in Goldberg, et al., ed. "Beyond webcams", MIT Press, Jan. 4, 2002, pp. 155-167.
Paulos, "Personal tele-embodiment", OskiCat Catalog Record, UCB Library Catalog, 2001, 3 pages.
Paulos, "Personal Tele-Embodiment", Introductory and cover pages from 2001 Dissertation including Contents table, together with e-mails relating thereto from UC Berkeley Libraries, as shelved at

(56) References Cited

OTHER PUBLICATIONS

UC Berkeley Engineering Library (Northern Regional library Facility), May 8, 2002, 25 pages, including 4 pages of e-mails.
Paulos, et al., "Social Tele-Embodiment: Understanding Presence", Autonomous Robots, vol. 11, Issue 1, Kluwer Academic Publishers, Jul. 2001, pp. 87-95.
Adams, "Mobile Robotics Research Group", Mobile Robotics Research Group, Edinburgh University, http://www.dai.ed.ac.uk/groups/mrg/MRG.html, Internet, Edinburgh. duplicate of 575084, 2000, pp. 1-2.
Ando, et al., "A Multimedia Self-service Terminal with Conferencing Functions", IEEE, Jul. 5-7, 1995, pp. 357-362.
Android Amusement Corp., "What Marketing Secret . . . Renting Robots from Android Amusement Corp!", (Advertisement), 1982.
Apple, Inc., "iPhone", iPhone Series, XP002696350, http://en.wikipedia.org/wiki/IPhone_5, n. d., retrieved Apr. 30, 2013, pp. 1-29.
Applebome, "Planning Domesticated Robots for Tomorrow's Household", New York Times, http://www.theoldrobots.com/images17/dc17.JPG, Mar. 4, 1982, pp. 21,23.
Bar-Cohen, et al., "Virtual reality robotic telesurgery simulations using MEMICA haptic system", Internet, Mar. 5, 2001, pp. 1-7.
Barrett, "Video Conferencing Business Soars as Companies Cut Travel; Some Travel Cuts Are Permanent", http://www.ivci.com/international_videoconferencing_news_videoconferencing_news_19.html, Mar. 13, 2002.
Bartholomew, "An Apothecary's Pharmacy", http://classes.bnf.fr/ema/grands/034.htm, National Library of France, BnF-Teaching Kit-Childhood in the Middle Ages, Encyclopedic reference entry from Bartholomew of England, Book of the Properties of Things, France, Late XVth Century Paris, BnF, Manuscripts Department, 218 French, fol. 111, no date.
Bauer, et al., "Service Robots in Health Care: The Evolution of Mechanical Solutions to Human Resource Problems", Jun. 2003.
Bauer, et al., "Remote telesurgical mentoring: feasibility and efficacy", IEEE, 2000, pp. 1-9.
Bischoff, "Design Concept and Realization of the Humanoid Service Robot HERMES", Field and Service Robotics, Springer, London, 1998, pp. 485-492.
Blackwell, "Video: A Wireless LAN Killer App?", Internet, Apr. 16, 2002, pp. 1-3.
Blaer, et al., "TopBot: Automated Network Topology Detection With a Mobile Robot", Proceedings of the 2003 IEEE International Conference on Robotics 7 Automation, Taipei, Taiwan, Sep. 14-19, 2003, pp. 1582-1587.
Bradner, "The Internet Standards Process—Revision 3", Network Working Group Request for Comments: 2026, www.rfc-e ditor.org!rfC/rfc2026. txt, Oct. 1996, pp. 1-36.
Breslow, et al., "Effect of a multiple-site intensive care unit telemedicine program on clinical and economic outcome an alternative paradigm for intensivist staffing", Critical Care Med; vol. 32 No. 1, Jan. 2004, pp. 31-38.
Brooks, "Remote Presence", Abstracts from Flesh & Machines, How Robots Will Change Us, Feb. 2002, pp. 131-147.
Brooks, "A Robust Layered Control System for a Mobile Robot," IEEE Journal of Robotics and Automation, 2 (1), Mar. 1986, 10 pgs.
Candelas, et al., "Flexible virtual and remote laboratory for teaching Robotics", FORMATEX 2006; Proc. Advance in Control Education Madrid, Spain, Jun. 2006, pp. 21-23.
Celi, et al., "The EICU: It's not just telemedicine", Critical Care Medicine vol. 29, No. 8 (Supplement), Aug. 2001.
Cheetham, et al., "Interface Development for a Child's Video Conferencing Robot", 2000, pp. 1-4.
Christensen et al., "BeeSoft User's Guide and Reference", Robots for the Real World™, Real World Interface, Inc., www.praecogito.com/-brudy/zaza/BeeSoft-manual-1.2-2/ beeman~1.htm, Sep. 26, 1997, pp. 1-203.
Cleary, et al., "State of the art in surgical robotics: Clinical applications and technology challenges", Internet, Feb. 24, 2002, pp. 1-26.

CNN, "Floating 'droids' to roam space corridors of the future", Internet, Jan. 12, 2000, pp. 1-4.
cnn.com/technology, "Paging R.Robot: Machine helps doctors with patients", Internet, Sep. 30, 2003, pp. 1-3.
Crowley, "Hello to Our Future", AARP Bulletin, http://www.cs.cmu.ed/-nursebot/web/press/aarp 99_14/millennium.html, Jan. 2000.
Dalton, "Techniques for Web Telerobotics", PhD Thesis, University of Western Australia, http://telerobot.mech.uwa.edu.au/information.html, http://catalogue.library.uwa.edu.au/search, 2001, pp. 27-62 149-191.
Dario, "A Robot Workstation for Diagnosis and Physical Therapy", IEEE Catalog No. 88TH0234-5, 1989, pp. 67-72.
Davies, "Robotics in Minimally Invasive Surgery", Mechatronics in Medicine Lab, Dept Mechanical Engineering, Imperial College, London SW7 2BX, The Institution of Electrical Engineers, IEE, Savoy Place, London WC2R OBL, UK, 1995, pp. 5/1-5/2.
Davis, "Meet iRobot, The Smartest Webcam on Wheels," Wired Magazine, 8.09, http://www.wired.com/wired/archive/8.09/irobot_pr.html, Sep. 2000, 2 pgs.
Dean, et al., "1992 AAAI Robot Exhibition and Competition," AI Magazine, Spring 1993, 10 pgs.
Defendant VGo Communications, Inc.'s Invalidity Contentions Pursuant to the Feb. 27, 2012 Civil Minute Order, May 2, 2012.
Defendant-Counterclaimant VGo Communications, Inc.'s Supplemental Invalidity Contentions Pursuant to the Feb. 27, 2012 Civil Minute Order, May 14, 2012.
DiGiorgio, "Is Your Emergency Department of the Leading Edge?", Internet, 2005, pp. 1-4.
Discovery Channel Canada, "Inventing the Future: 2000 Years of Discovery", http://www.sfwriter.com/pritf.htm, (Video Transcript), Jan. 2, 2000.
Dudenhoeffer, et al., "Command and Control Architectures for Autonomous Micro-Robotic Forces", http://www.inl.gov/technicalpublications/Documents/3157051.pdf, Apr. 2001.
Elhajj, et al., "Supermedia in Internet-based telerobotic operations", Internet, 2001, pp. 1-14.
Elhajj, et al., "Synchronization and Control of Supermedia Transmission Via the Internet", Proceedings of 2001 International Symposium on Intelligent Multimedia Video and Speech Processing., Hong Kong, May 2-4, 2001.
Elhajj, "Real-Time Haptic Feedback in Internet-Based Telerobotic Operation", IEEE International Conference on Electro/Information Technology, http://www.egr.msu.edu/~ralab-web/cgi_bin/internet-teleoperation.php, Jun. 2000.
Ellison, et al., "Telerounding and Patient Satisfaction Following Surgery", pp. 523-530.
Fels, "Developing a Video-Mediated Communication System for Hospitalized Children", Telemedicine Journal, vol. 5, No. 2, 1999.
Fetterman, "Videoconferencing over the Internet", Internet, 2001, pp. 1-8.
Fiorini, et al., "Health Care Robotics: A Progress Report", IEEE International Conference on Robotics and Automation, 1997., Apr. 1997, pp. 1271-1276.
Fong, "Collaborative Control: A Robot-Centric Model for Vehicle Teleoperation", The Robotics Institute Carnegie Mellon University, http://web.archive.org/web/20030504040803/www.ricmu.edu/cgi-bin/tech_reports.cgi?year=2001&text=0, Nov. 2001.
Ghiasi, et al., "A Generic Web-based Teleoperations Architecture: Details and Experience", SPIE Conference on Telemanipulator and Telepresence Technologies VI, Sep. 1999.
Goldberg, et al., "Collaborative Teleoperation via the Internet", IEEE International Conference on Robotics and Automation, San Francisco, California, Apr. 2000.
Goldberg, "Desktop Teleoperation via the World Wide Web, Proceedings of the IEEE International Conference on Robotics and Automation", http://citeseer.ist.osu.edu/cache/oaoers/cs/5/fto:zSzzSzusc.eduzSzoubzSziriszSzraiders.odf/aol, 1995, pp. 654-659.
Goldberg, "More Online Robots: Robots that Manipulate", Internet Robots, Updated Aug. 2001, http://ford.ieor.berkeley.edu/ir/robots_a2.html, Aug. 2001, pp. 1-3.
Goldenberg, et al., "Telemedicine in Otolaryngology", American Journal of Otolaryngology vol. 23,No. 1, 2002 , pp. 35-43.

(56) References Cited

OTHER PUBLICATIONS

Goldman, "Machine Dreams", Entrepreneurs, Forbes, May 27, 2002.
Gostai, "Robotic Telepresence: Gostai Jazz", Flyer, http://www.gostai.com, n. date, 4 pgs.
Grow, "Office Coworker Robot," Time Magazine, http://www.time.com/time/specials/packages/article/0,28804,1936165_1936255_1936640,00.html, Nov. 19, 2001, 2 pgs.
Gump, "Robot Technology Improves VA Pharmacies", Internet, 2001, pp. 1-3.
Hameed, et al., "A Review of Telemedicine", Journal of Telemedicine and Telecare., vol. 5, Supplement 1, 1999, pp. S1:103-S1:106.
Han, et al., "Construction of an Omnidirectional Mobile Robot Platform Based on Active Dual-Wheel Caster Mechanisms and Development of a Control Simulator", Kluwer Acedemic Publishers, vol. 29, Nov. 2000, pp. 257-275.
Handley, et al., "RFC 2327—SDP: Session Description Protocol", http://www.faqs.org/rfcs/rfc2327.html, Apr. 1998.
Hanebeck, et al., "ROMAN: A mobile Robotic Assistant for Indoor Service Applications", Proceedings of the 1997 IEEE/RSJ International Conference on Intelligent Robots and Systems, 1997.
Harmo, et al., "Moving Eye—Interactive Telepresence Over Internet With a Ball Shaped Mobile Robot", 2000.
Haule, et al., "Control Scheme for Delayed Teleoperation Tasks", Proceedings of the Pacific Rim Conference on Communications, Computer and Signal Processing, May 17, 1995.
Hees, "Communications Design for a Remote Presence Robot", Jan. 14, 2002.
Holmberg, "Development of a Holonomic Mobile Robot for Mobile Manipulation Tasks", International Conference on Field and Service Robotics, Pittsburgh, PA, Aug. 1999.
Ishiguro, "Integrating a Perceptual Information Infrastructure with Robotic Avatars: A Framework for Tele-Existence", Proceeding of IEEE Conference on Intelligent Robots and Systems, 1999, pp. 1032-1038.
Ishihara, et al., "Intelligent Microrobot DDS (Drug Delivery System) Measured and Controlled by Ultrasonics", IEEE/RSJ, vol. 2, Nov. 3-5, 1991, pp. 1145-115.
ITU, "ITU-T H.281 A Far End Camera Control Protocol for Videoconferences using H.224", http://www.itu.int/rec/T-RECH.281-199411-I/en, Nov. 1994.
ITU, "ITU-T H.323 Packet-based multimedia communications", http://www.itu.int/rec/T-REC-H.323-199802-S/en, Feb. 1998.
ITU, "ITU-T H.450.11 Call Intrusion Supplementary Service for H.323", http://www.itu.int/rec/T-RECH.450.11-200103-I/en, Mar. 2001.
ITU, "ITU-T H.450.9 Call Completion Supplementary Services for H.323", http://www.itu.int/rec/T-RECH.450.9-200011-I/en, Nov. 2000.
Ivanova, Master's thesis: Internet Based Interface for Control of a Mobile Robot, Department of Numerical Analysis and Computer Science, 2003, 59 pgs.
Jenkins, et al., "Telehealth Advancing Nursing Practice", Nursing Outlook, vol. 49, No. 2, Mar./Apr. 2001.
Johanson, "Supporting video-mediated communication over the Internet", Chalmers University of Technology,Dept of Computer Engineering, Gothenburg, Sweden, 2003.
Jouppi, et al., "Mutually-Immersive Audio Telepresence", Audio Engineering Society Convention Paper presented at 113th Convention, Oct. 2002.
Jouppi, et al., "First Steps Towards Mutually-Immersive Mobile Telepresence", CSCW, 02, New Orleans LA, Nov. 16-20, 2002.
Kanehiro, et al., "Virtual Humanoid Robot Platform to Develop Controllers of Real Humanoid Robots without Porting", IEEE, 2001, pp. 3217-3276.
Kaplan, et al., "An Internet Accessible Telepresence", {aek keshav nls jhv}@research.att.com, AT&T Bell Laboratories, Murray Hill, N.J., pp. 1-7.
Keller, et al., "Raven Interface Project", Fall 2001, http://upclose.lrdc.pitt.edu/people/louw_assets/Raven_Slides.pps , Fall 2001.
Khatib, "Robots in Human Environments", Proc. International Conference on Control, Automation, Robotics, and Vision ICRACV2000, Singapore, Dec. 2000, pp. 454-457.
Knight, et al., "Active Visual Alignment of a Mobile Stereo Camera Platform", Proceedings of the IEEE, International Conference on Robotics and Automation, San Francisco, Apr. 24-28, 2000, pp. 3202-3208.
Kuzuoka, et al., "Can the GestureCam Be a Surrogate?", Proceedings of the Fourth European Conference on Computer-Supported Cooperative Work, Sep. 10-14, pp. 181-196.
Lane, "Automated Aides", Newsday, http://www.cs.cum.edu/nursebot/web/press/nd4380.htm, Oct. 17, 2000.
Lee, et al., "A novel method of surgical instruction: International telementoring", Internet, 1998, pp. 1-4.
Leifer, et al., "VIPRR: A Virtually in Person Rehabilitation Robot", Proceedings of 1997 International Conference on Rehabilitation Robotics, http://www.stanford.edu/group/rrdlPeople/vdl/publicationsIICORR97/VIPRR.html, Apr. 14-15, 1997, 4 pgs.
Lim, et al., "Control to Realize Human-like Walking of a Biped Humanoid Robot", IEEE, 2000, pp. 3271-3276.
Linebarger, et al., "Concurrency Control Mechanisms for Closely Coupled Collaboration in Multithreaded Virtual Environments", Presence, Special Issue on Advances in Collaborative VEs, 2004.
Loeb, et al., "Virtual Visit: Improving Communication for Those Who Need It Most", Stud Health Technol Inform.; 94: 302-8., 2003.
Long, "HelpMate Robotics, Inc. (Formerly Transitions Research Corporation) Robot Navigation Technology", NIST Special Publication, http://www.atp.nist.gov/eao/sp950-1/helpmate.htm, Mar. 1999, pp. 950-951.
Luna, "Robot a new face on geriatric care", OC Register, 8-6, 2003.
Mack, "Minimally invasive and robotic surgery", Internet IEEE, 2001, pp. 568-572.
Mair, "Telepresence—The Technology. And Its Economic and Social Implications", IEEE Technology and Society, 1997.
Martin, "Days Ahead", Assisted Living Today, vol. 9, Nov./Dec. 2002, pp. 19-22.
McCardle, et al., "The challenge of utilizing new technology in design education", Internet, 2000, pp. 122-127.
Meng, et al., "E-Service Robot in Home Healthcare", Proceedings of the 2000 IEEE/RSJ, International Conference on Intelligent Robots and Systems, 2000, pp. 832-837.
Metz, "HP Labs", PCMAG.com, http://www.pcmag.com/article2/0,2817,1130820,00.asp, Jul. 1, 2003.
Michaud, "Introducing Nursebot", The Boston Globe, http://www.cs.cmu.edu/nursebot/web/press/globe 3 01/index.html, Sep. 11, 2001, pp. 1-5.
Minsky, "Telepresence", OMNI, Jun. 1980, pp. 1-6.
Montemerlo, "Telepresence: Experiments in Next Generation Internet", CMU Robotics Institute, http://www.ri.cmu.edu/creative/archives.htm (Video/Transcript), Oct. 20, 1998.
Motorola Technical Developments, et al., "Detection of Target Mobile Signal Strength", PriorArt Database: Technical Disclosure, IP.com, Retrieved from http:www.ip.com/pubview/IPCOM000009024D, original publication date: Jan. 1, 1999 by Motorola, Inc., pp. 205-206, Aug. 1, 2002, pp. 1583-1587.
Murphy, "Introduction to A1 Robotics", A Bradford Book, 2000, p. 487.
Nakajima, et al., "A Multimedia Teleteaching System using an Electronic Whiteboard for Two Way Communication of Motion Videos and Chalkboards", IEEE, 1993, pp. 436-441.
National Energy RES SCI COMP CTR, "Berkeley Lab's RAGE Telepresence Robot Captures R&D100 Award", http://www.nersc.gov/news/newsroom/RAGE070202.php, Jul. 2, 2002.
Nomadic Technologies Inc., "Nomad XR4000 Hardware Manual", Release 1.0, Mar. 1999.
Noritsugu, "Application of Rubber Artificial Muscle Manipulator as a Rehabilitation Robot", IEEE/ASME Transations on Mechatronics, vol. 2, No. 4, Dec. 1997, pp. 259-267.
Ogata, et al., "Development of Emotional Communication Robot: WAMOEBA-2r-Experimental Evaluation", IEEE, 2000, pp. 175-180.

(56) References Cited

OTHER PUBLICATIONS

Ogata, et al., "Emotional Communication Robot: WANOEBA-2R—Emotion Model and Evaluation Experiments", Internet, 1999, pp. 1-16.
Oh, et al., "Autonomous Battery Recharging for Indoor Mobile Robots", Proceedings of Australian Conference on Robotics and Automation, http://users.rsise.anu.edu.au/rsl/rsl_papers/ACRA2000/Auto_Recharge_Paper.pdf, 2000.
Ojha, "An application of Virtual Reality in Rehabilitation", IEEE, Apr. 10-13, 1994, pp. 4-6.
Osborn, "QoLT Research Overview", Quality of Life Technology Center:A National Science Foundation Engineering Research Center, Carnegie Mellon University of Pittsburgh, www.qolt.org, n. date, 2 pgs.
Paulos, et al., "A World Wide Web Telerobotic Remote Environment Browser", http://vive.cs.berkeley.edu/capek, 1995.
Paulos, et al., "Ubiquitous Tele-embodiment: Applications and Implications", International Journal of Human Computer Studies, vol. 46, No. 6, Jun. 1997, pp. 861-877.
Paulos, "Designing Personal Tele-embodiment", IEEE International Conference on Robotics and Automation http://www.prop.org/papers/icra98.pdf, 1998.
Paulos, "Personal Tele-Embodiment", UC Berkeley, Fall 2001.
Paulos, "PRoP: Personal Roving Presence", ACM:CHI Proceedings of CHI '98, http://www.prop.org/papers/chi98.pdf, 1998, p. 6.
Paulos, "Video of PRoP 2 at Richmond Field Station", www.prop.org Printout of Home Page of Website and two-page Transcript of the audio portion of said PRoP Video, May 2001.
PictureTel Adds New Features and Functionality to Its Award-Winning Live200 Desktop Videoconferencing System, PR Newswire Association, LLC, Gale, Cengage Learning, http://www.thefreelibrary.com/PictureTel+Adds+New+Features+And+Functionality+To+Its+Award-Winning...-a019512804, Jun. 13, 1997.
PictureTel, "PictureTel Live200 for Windows NT Product Guide", http://support.polycom.com/global/documents/support/user/products/video/live200_live200NT_product_guide.pdf, Nov. 1994.
Pin, et al., "A New Family of Omnidirectional and Holonomic Wheeled Platforms for Mobile Robots", IEEE, vol. 10, No. 4, Aug. 1994.
Reynolds et al., "Review of Robotic Telemedicine Utilization in Intensive Care Units (ICUs)", 11th Annual ATA Symposium, Tampa, Florida, 2011, 1 pg.
Roach, "Automatic Call Back Service in SIP", http://tools.ietf.org/pdf/draftroach-sip-acb-00.pdf, Mar. 2000.
Rovetta, et al., "A New Telerobotic Application: Remote Laparoscopic Surgery Using Satellites and and optical fiber Networks for Data Exchange", International Journal of Robotics Research, Jun. 1, 1996, pp. 267-279.
Roy, et al., "Towards Personal Service Robots for the Elderly", Internet, Mar. 7, 2002, 7 pgs.
Salemi, et al., "MILO: Personal robot platform", Internet, 2005, pp. 1-6.
Sandt, et al., "Perceptions for a Transport Robot in Public Environments", IROS, 1997.
"Saphira Software Manual", Saphira Version 5.3, ActiveMedia, Inc., 1997, 105 pgs.
Schaeffer, "Care-O-bot: A System for Assisting Elderly or Disabled Persons in Home Environments", Proceedings of AAATE-99, http://morpha.de/download/publications/IPA, 1999.
Schulz, et al., "Web Interfaces for Mobile Robots in Public Places", Robotics & Automation Magazine, IEEE, vol. 7, Issue 1, Mar. 2000, pp. 1-9.
Shimoga, et al., "Touch and force reflection for telepresence surgery", IEEE, 1994, pp. 1049-1050.
Siegwart, "Interacting Mobile Robots on the Web", Proceedings of the 1999 IEEE International Conference on Robotics and Automation, May 1999.
Simmons, "Xavier: An Autonomous Mobile Robot on the Web", IEEE Robotics and Automation Magazine, 1999, pp. 43-48.
Spawar Systems Center, "Robart", San Diego, CA, http://www.nosc.mil/robots/land/robart/robart.html, 1998, pp. 1-8.
Stephenson, "Dr. Robot Tested at Hopkins", Internet, Aug. 5, 2003, pp. 1-2.
Stoianovici, et al., "Robotic Tools for Minimally Invasive Urologic Surgery", Internet, Dec. 2002, pp. 1-17.
Summers, "Microsoft NetMeeting 3 Features excerpt from Official Microsoft NetMeeting 3.0 Book", http://technet.microsoft.com/en-us/library/cc723477.aspx#XSLTsection121121120120, excerpt from Microsoft Press http://www.computerbooksonline.com/abook.asp?i=0735605823, Mar. 1999.
Suplee, "Mastering the Robot", The Washington Post, http://www.cs.cmu.edu-nursebotlweb/press/wash/index.html, Sep. 17, 2000, p. A01.
Tahboub, et al., "Dynamics Analysis and Control of a Holonomic Vehicle With Continously Variable Transmission", Journal of Dynamic Systems, Measurement and Control ASME vol. 124, Mar. 2002, pp. 118-126.
Tendick, et al., "Human-Machine Interfaces for Minimally Invasive Surgery", IEEE, 1997, pp. 2771-2776.
Thrun, et al., "Probabilistic Algorithms and the Interactive Museum Tour-Guide Robot Minerva", Internet, 2000, pp. 1-35.
Tipsuwan, et al., "Gain Adaptation of Networked Mobile Robot to Compensate QoS Deterioration", IEEE, 2000, pp. 3146-3151.
Tsui, et al., "Exploring Use Cases for Telepresence Robots", Human-Robot Interaction, Lausanne, Switzerland, http://robotics.cs.uml.edu/fileadmin/content/publications/2011/tsui-et-al-telepresence-HRI11.pdf, Robotics Lab UMass Lowell, 2011, 7 pgs.
Tzafestas, et al., "VR-based Teleoperation of a Mobile Robotic Assistant: Progress Report", Technical Report DEMO 2000/13, Institute of Informatics and Telecommunications, National Center for Scientific Research "Demokritos", Athens, Greece, Nov. 2000, pp. 1-23.
UMASS Lowell Robotics Lab, "Robotics Lab @ UMASS Lowell", Brochure, http://robotics.cs.uml.edu/fileadmin/content/brochures/roboticslab_brochure_2011_WEB.pdf, 2011, 2 pgs.
U.S. Appl. No. 10/783,760, filed Feb. 20, 2004, Wang, et al., 48 pgs.
U.S. Appl. No. 60/449,762, filed Feb. 24, 2003, Wang, et al., 28 pgs.
Urquhart, "InTouch's robotic Companion 'beams up' healthcare experts", Medical Device Daily, vol. 7, No. 39, Feb. 27, 2003, pp. 1,4.
Video Middleware Group, "H.350 Directory Services for Multimedia", http://www.vide.net/resources/h350vendor.pdf, n. date, 2 pgs.
Weiss, et al., "Telework and video-mediated communication: Importance of real-time, interactive communication for workers with disabilities", California State University Northridge http://www.csun.edu/cod/conf/1999/proceedings/session0238.html, pp. 1-4.
Weiss, et al., "PEBBLES: A Personal Technology for Meeting Education, Social and Emotional Needs of Hospitalised Children", Personal and Ubiquitous Computing 5, Springer-Verlag London Ltd., 2001, pp. 157-168.
West, et al., "Design of Ball Wheel Mechanisms for Omnidirectional Vehicles with Full Mobility and Invariant Kinematics", Journal of Mechanical Design, vol. 119, Jun. 1997, pp. 153-161.
Yamasaki, et al., "Applying Personal Robots and Active Interface to Video Conference Systems", Internet, 1995, pp. 243-248.
Yamauchi, "PackBot: A Versatile Platform for Military Robotics", Internet, 2004, pp. 1-10.
Yong, et al., "Robot task execution with telepresence using virtual reality technology", Internet, 1998, pp. 1-8.
Zambroski, "CMU, Pitt Developing 'nursebot'", http://www.cs.cmu.edu/~nursebot/web/press/tribunereview.html, Oct. 27, 2000.
Zamrazil, "Telemedicine in Texas: Public Policy Concerns", House Research Organization Focus Report, Texas House of Representatives, http://www.hro.house.state.tx.us/focus/telemed.pdf, May 5, 2000, pp. 76-22.
Zipperer, "Robotic dispensing system", ISMP Medication Safety Alert! vol. 4, Issue 17, Aug. 25, 1999, pp. 1-2.
Zorn, "Ubiquitous Telepresence", http://www.cs.colorado.edu/~zorn/utivision/vision.html, Mar. 3, 1996.
Nomadic Technologies, Inc., "Nomad Scout User's Manual", Software Version 2.7, Part No. DOC00004, Jul. 12, 1999, pp. 1-59.

(56) References Cited

OTHER PUBLICATIONS

ACM Digital Library Record, Autonomous Robots, vol. 11, No. 1, Table of Content, available at <http://dl.acm.org/citation.cfm?id=591550&picked=prox&cfid=360891374&cftoken=35225929>, Jul. 2001, 2 pages.

Brenner, Pablo, "A Technical Tutorial on the IEEE 802.11 Protocol", BreezeCOM Wireless Communications, Jul. 18, 1996, pp. 1-24.

Library of Congress, "008-Fixed-Length Data Elements (NR)", MARC 21 Format for Classification Data, available at <http://www.loc.gov/marc/classification/cd008.html>, retrieved on Jul. 22, 2014, pp. 1-14.

Paulos et al., "Personal Tele-Embodiment", Chapter 9 in Goldberg et al., Ed., "Beyond Webcams", MIT Press, Jan. 4, 2002, pp. 155-167.

Paulos et al., "Social Tele-Embodiment: Understanding Presence", Autonomous Robots, vol. 11, No. 1, Kluwer Academic Publishers, Jul. 2001, pp. 87-95.

Paulos, Eric John, "Personal Tele-Embodiment", Introductory and Cover Pages from 2001 Dissertation Including Contents table, together with E-mails Relating thereto from UC Berkeley Libraries, as Shelved at UC Berkeley Engineering Library (Northern Regional Library Facility), May 8, 2002, 25 pages (including 4 pages of e-mails).

Paulos, Eric John, "Personal Tele-Embodiment", OskiCat Catalog Record, UCB Library Catalog, Results page and MARC Display, retrieved on Jun. 14, 2014, 3 pages.

* cited by examiner

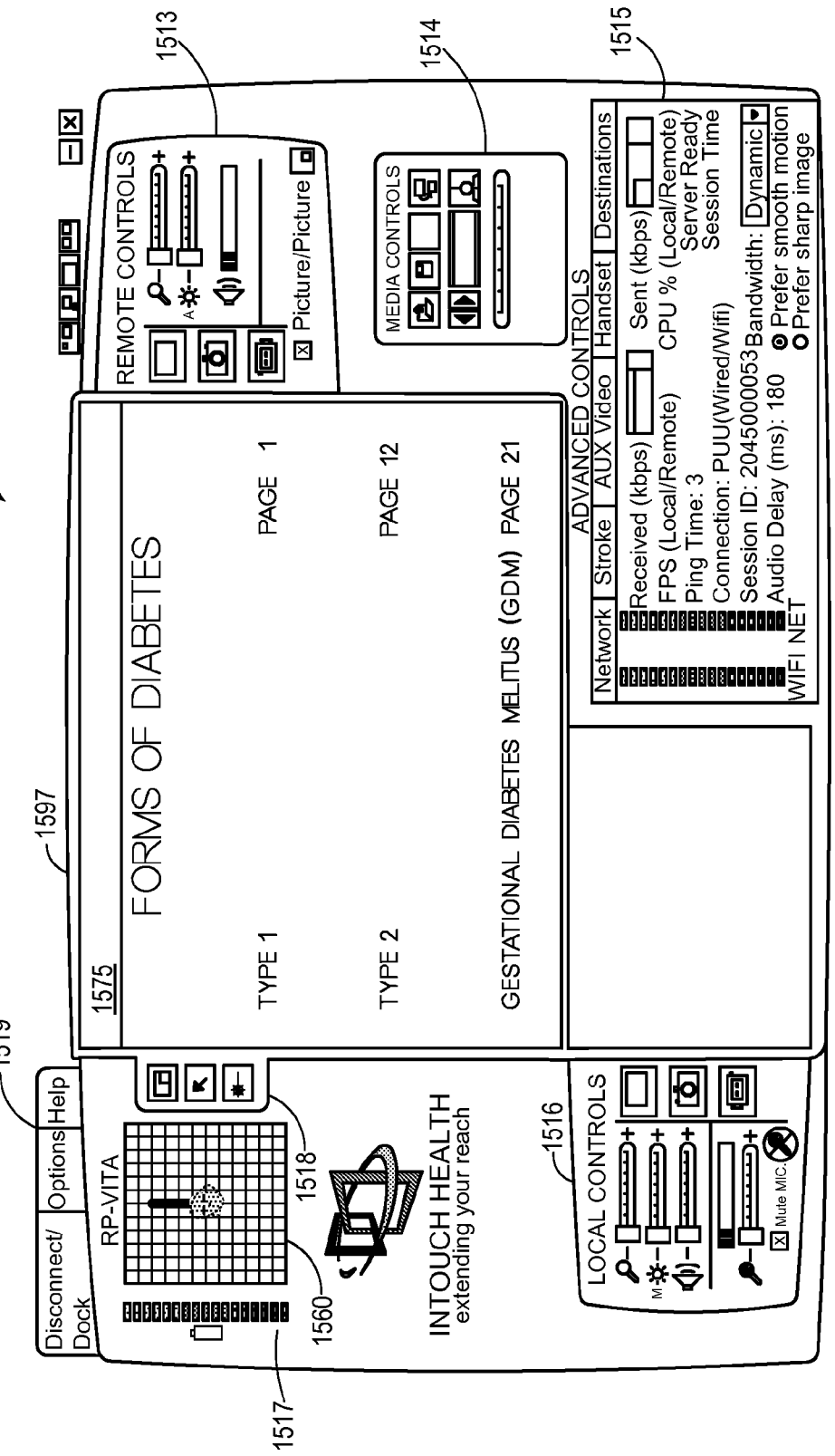

ENHANCED VIDEO INTERACTION FOR A USER INTERFACE OF A TELEPRESENCE NETWORK

RELATED APPLICATIONS

This U.S. patent application claims priority under 35 U.S.C. §119(e) to U.S. Provisional Application No. 61/729,964 filed Nov. 26, 2012, titled "ENHANCED DIAGNOSTICS USING MULTIPLE SENSORS WITH COORDINATED SENSOR SPACES," which application is hereby incorporated by reference in its entirety.

TECHNICAL FIELD

This disclosure relates to enhanced interactive and display interfaces for a telepresence device. More specifically, this disclosure relates to systems and methods for improving user access and understanding of spatially and/or temporally disparate information contained in saved video captured by a telepresence device.

BRIEF DESCRIPTION OF THE DRAWINGS

Non-limiting and non-exhaustive embodiments of the disclosure are described herein, including various embodiments of the disclosure illustrated in the figures listed below.

FIG. 15D illustrates a zoomed view of the document with the text deskewed and rotated.

Figure 1:
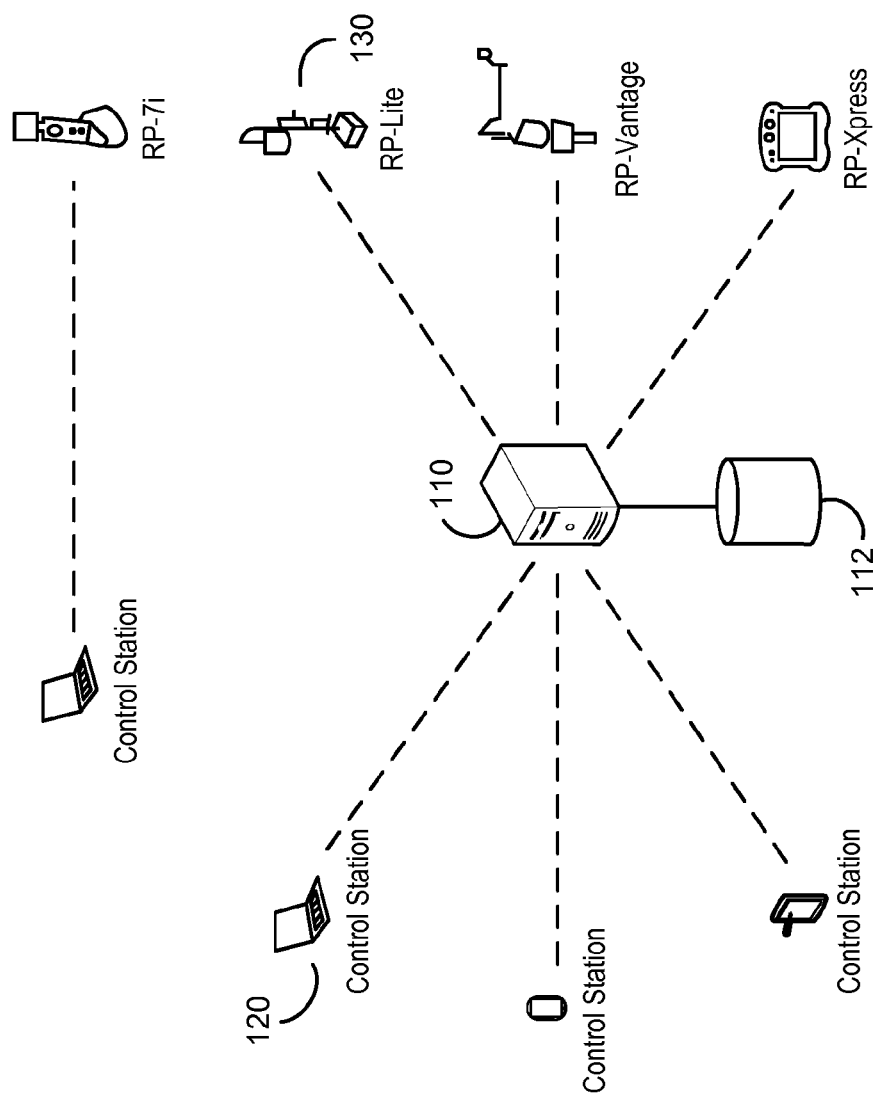
FIG. 1 is a schematic diagram of a telepresence network comprising a plurality of telepresence devices.

The described features, structures, and/or characteristics of the systems and methods described herein may be combined in any suitable manner in one or more alternative embodiments, and may differ from the illustrated embodiments.

DETAILED DESCRIPTION OF PREFERRED EMBODIMENTS

A telepresence device may be part of a telepresence network that allows users remote from the telepresence device to interact with an environment where the telepresence device is located. The telepresence device may be configured to capture video and/or environmental measurements, which may be relayed to one or more users. A control device may allow the one or more users to interact with the telepresence device, such as by sending and/or receiving captured video and/or audio, sending commands to the telepresence device, and the like. Each telepresence network may include one or more facilities that each include at least one corresponding telepresence device local to the facility. Exemplary facilities may include manufacturing plants, research and development facilities, testing facilities, hospitals, rehabilitation facilities, long-term care facilities, and the like. Types of telepresence devices include, but are not limited to, remote telepresence devices, mobile telepresence units, and/or control stations. For example, a remote telepresence device may include a telepresence robot configured to move within a medical facility and provide a means for a remote practitioner to perform remote consultations.

Exemplary, non-limiting uses for telepresence devices may include healthcare and industrial applications. For example, healthcare facilities may include telemedicine technologies, such as telepresence devices in a telepresence network, that allow remote healthcare practitioners to provide services to patients and/or other healthcare practitioners in remote locations. A remote medical professional may be a neurologist practicing in a relatively large hospital who may, via a telepresence device, provide services and consultations to patients and/or other medical professionals in hospitals located in rural areas that otherwise may not have a neurologist on staff.

The control device may include a general purpose and/or special purpose computer systems and/or one or more computer networks. In an embodiment, the control device and the telepresence device may each include at least one camera, at least one display device, at least one speaker, and at least one microphone to allow for two-way video/audio communication. One or more input devices may allow the user of the control device to remotely control movement of the telepresence device. Additional discussion of remotely controlling movement of a telepresence device is contained in U.S. Pat. No. 6,845,297, titled "Method and System for Remote Control of Mobile Robot," filed on Jan. 9, 2003, and European Patent No. 1279081, titled "Method and System for Remote Control of Mobile Robot," filed on May 1, 2001, which applications are hereby incorporated by reference in their entireties.

The control device, the telepresence device, and/or the telepresence network may be configured to store session content data, such video and/or audio recordings, telemetry data, notes, time stamps, and/or the like. In an embodiment, the telepresence network may include a server configured to store the session content data. Additional discussion of data storage for telepresence devices and automatic use of stored data is contained in U.S. patent application Ser. No. 12/362,454, titled "DOCUMENTATION THROUGH A REMOTE PRESENCE ROBOT," filed on Jan. 29, 2009, which application is hereby incorporated by reference in its entirety.

Reference throughout this specification to "one embodiment" or "an embodiment" means that a particular feature, structure, or characteristic described in connection with the embodiment is included in at least one embodiment. Thus, the appearances of the phrases "in one embodiment" and "in an embodiment" in various places throughout this specification are not necessarily all referring to the same embodiment. In particular, an "embodiment" may be a system, an article of manufacture (such as a computer-readable storage medium), a method, and/or a product of a process.

The phrases "connected to" and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

The embodiments of the disclosure may be understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations and/or components are not shown or described in detail.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless otherwise specified.

Embodiments may include various steps, which may be embodied in machine-executable instructions to be executed by a computer system. The computer system may comprise one or more general-purpose or special-purpose computers (or other electronic devices). Alternatively, the computer system may comprise hardware components that include specific logic for performing the steps or comprise a combination of hardware, software, and/or firmware. Without limitation, a computer system may comprise a workstation, desktop computer, laptop computer, disconnectable mobile computer, server, mainframe, cluster, so-called "network computer" or "thin client," tablet, smartphone, multimedia device, electronic reader, personal digital assistant or other hand-held computing device, "smart" consumer electronics device or appliance, or a combination thereof. A server may include a physical server, a server cluster, a distributed server, a virtual server, a cloud server, a computer providing resources to one or more clients, a combination of one or more of the aforementioned, and/or the like. Some or all of the functions, steps, and/or operations discussed herein may be performed by one or more clients and/or one or more servers. Those of skill in the art will realize possible divisions of operations between the one or more servers and the one or more clients.

Each computer system includes at least a processor and a memory; computer systems may also include various input devices and/or output devices. The processor may include one or more general-purpose central processing units (CPUs), graphic processing units (GPUs), or Digital Signal Processors (DSPs), such as Intel®, AMD®, ARM®, Nvidia®, ATI®, TIC), or other "off-the-shelf" microprocessors. The processor may include a special-purpose processing device, such as an ASIC, PAL, PLA, PLD, Field Programmable Gate Array (FPGA), or other customized or programmable device. The memory may include static RAM, dynamic RAM, flash memory, ROM, CD-ROM, disk, tape, magnetic, optical, or other computer storage medium. The input device(s) may include a keyboard, mouse, touch screen, light or other pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computers may be capable of using a floppy drive, tape drive, optical drive, magneto-optical drive, memory card reader, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and predefined manner as described herein.

Embodiments may also be provided as a computer program product, including a non-transitory machine-readable storage medium having stored thereon instructions that may be used to program a computer system (or other electronic device) to perform processes described herein. The non-transitory machine-readable storage medium may include, but is not limited to, hard drives, floppy diskettes, optical disks, CD-ROMs, DVD-ROMs, ROMs, RAMs, EPROMs, EEPROMs, magnetic or optical cards, tapes, solid-state memory devices, or other types of media/machine-readable media suitable for storing electronic instructions.

Suitable networks for configuration and/or use as described herein include one or more local area networks, wide area networks, metropolitan area networks, and/or "Internet" or IP networks, such as the World Wide Web, a private Internet, a secure Internet, a value-added network, a virtual private network, an extranet, an intranet, or even standalone machines which communicate with other machines by physical transport of media (a so-called "sneakernet"). In particular, a suitable network may be formed from parts or entireties of two or more other networks, including networks using disparate hardware and network communication technologies. One suitable network includes a server and several clients; other suitable networks may contain other combinations of servers, clients, and/or peer-to-peer nodes, and a given computer may function both as a client and as a server. Each network includes at least two computer systems, such as the server and/or clients.

The network may include communications or networking software, such as the software available from Novell, Microsoft, Artisoft, and other vendors, and may operate using TCP/IP, SPX, IPX, and other protocols over twisted pair, coaxial, or optical fiber cables, telephone lines, satellites, microwave relays, modulated AC power lines, physical media transfer, and/or other data transmission "wires" known to those of skill in the art. The network may encompass smaller networks and/or be connectable to other networks through a gateway or similar mechanism.

Suitable software to assist in implementing the invention is readily provided by those of skill in the pertinent art(s) using the teachings presented here and programming languages and tools, such as Java, Pascal, C++, C, PHP, JavaScript, Python, C#, Perl, SQL, Ruby, Shell, Visual Basic, Assembly, Action Script, Objective C, Lisp, Scala, Tcl Haskell, Scheme, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer-executable code located within a memory device. A software module may, for instance, comprise one or more physical or logical blocks of computer instructions, which may be organized as a routine, a program, a script, an object, a component, a data structure, etc., that perform one or more tasks or implements particular abstract data types.

In certain embodiments, a particular software module may comprise disparate instructions stored in different locations of a memory device, different memory devices, or different computers, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that may be used according to the present invention is already available, such as general-purpose computers, computer programming tools and techniques, computer networks and networking technologies, and digital storage media.

FIG. 1 is a schematic diagram of a telepresence network 100 comprising a plurality of telepresence devices 130. A plurality of control devices 120, such as laptops, tablets, smart phones, and the like, may be configured to transmit video, audio, and/or commands to the telepresence devices 130 and receive video, audio, and/or measurement data from the telepresence devices 130. The control devices 120 may directly couple to the telepresence devices 130, and/or a server 110 may couple the control devices to the telepresence devices 130. In an embodiment, the server 110 may establish a connection between a control device 120 and a telepresence device 130, and the control device 120 and telepresence device 130 may communicate directly after the connection has been established. A connection between a control device 120 and a telepresence device 130 may be referred to as a session. The server 110 may comprise and/or be coupled to a hard drive 112. The hard drive 112 may be configured to store a history for one or more control devices 120 and/or telepresence devices 130. The history may include session data, commands, measurement data, recorded video and/or audio, annotations, bookmarks, and the like. The control devices 120 may be able retrieve the history from the hard drive 112 via the server 110.

Figure 2:
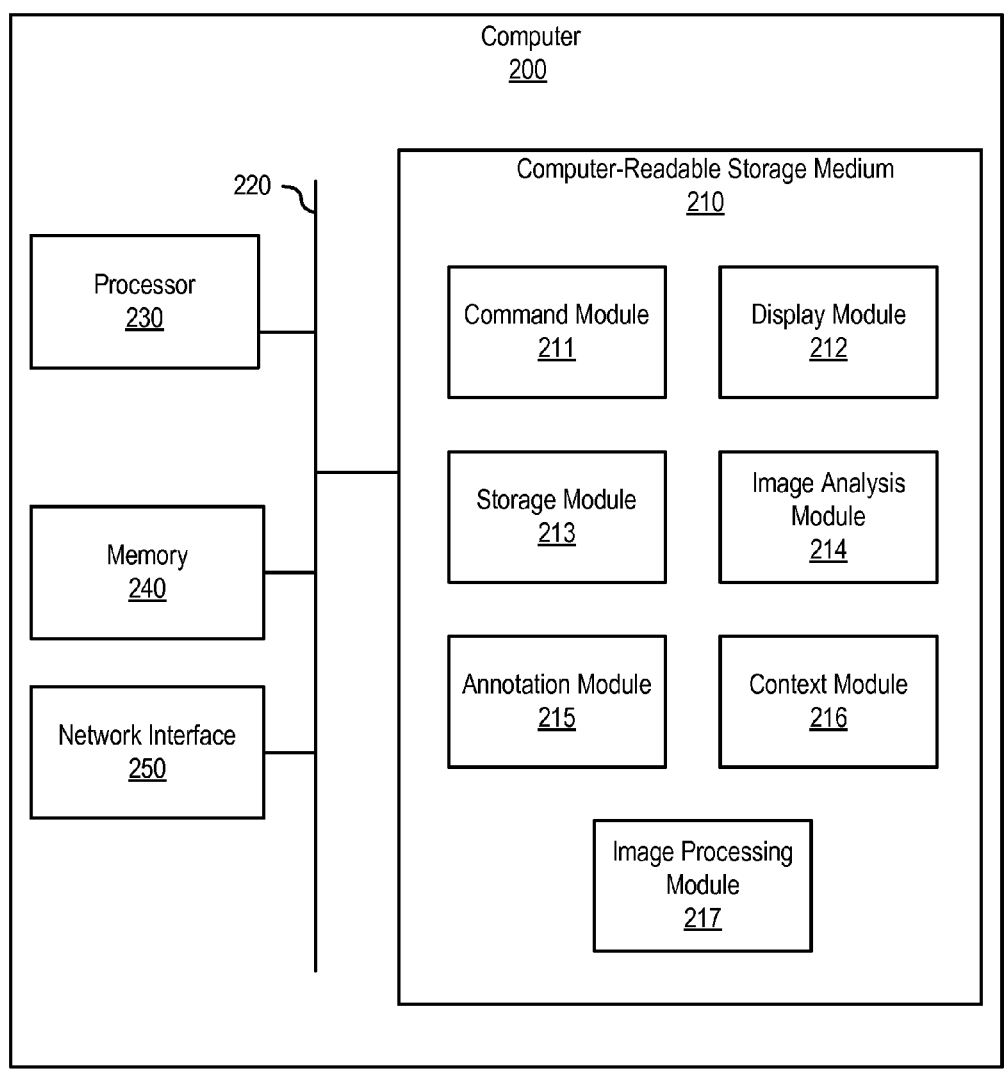
FIG. 2 is a schematic diagram of a computer configured to provide enhance video interaction.

FIG. 2 is a schematic diagram of a computer 200 configured to provide enhance video interaction. The computer 200 may include a processor 230 coupled to a volatile memory 240, a network interface 250, and a computer-readable storage medium 210 by a bus 220. In some embodiments, the computer-readable storage medium 210 may comprise the volatile memory 240. The computer-readable storage medium 210 may include a plurality of modules configured to perform specific functions, such as a command module 211 configured to deliver commands to a telepresence device, a display module 212 configured to provide a user interface for a user, a storage module 213 configured to store selected video, audio, and/or data, an image analysis module 214 configured to identify objects of interest in an image, an events module 215 configured to store events corresponding to time spans in videos, a context module 216 configured to store and search situational data, and an image processing module 217 edit, modify, and/or overlay images on a video. Alternatively, the computer 200 may contain more or fewer modules and/or a different computer may contain some of the modules.

Figure 3B:
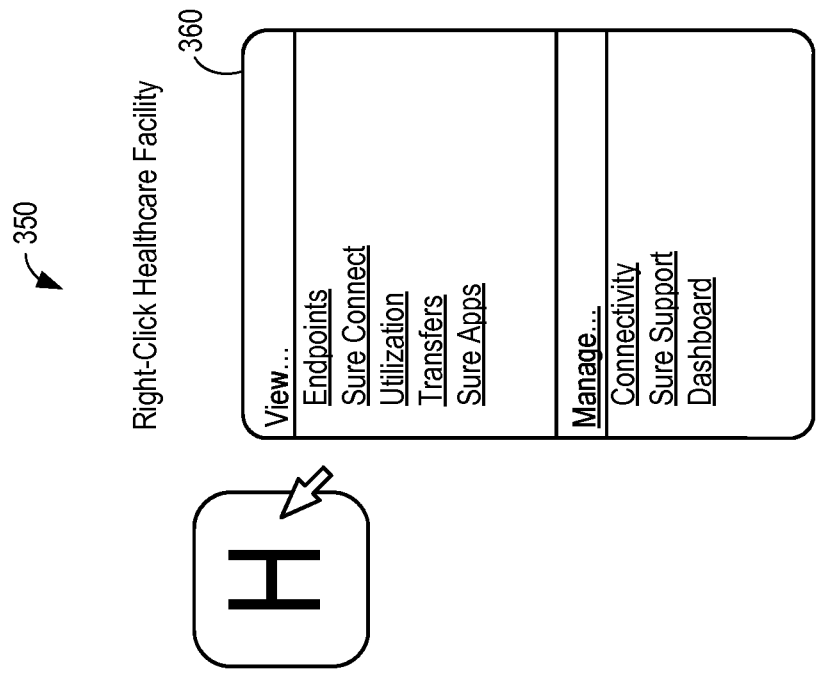
FIGS. 3A,B are exemplary screen displays that may be displayed to a user of a control device.
Figure 3A:
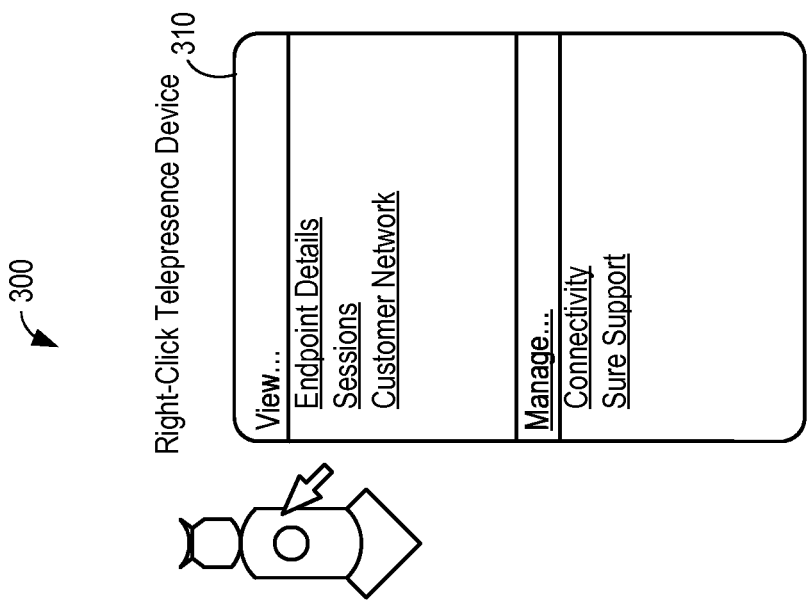

FIGS. 3A,B are exemplary screen displays 300, 350 that may be displayed to a user of a control device. The user may be attempting to connect to a telepresence device. A plurality of options 310, 360 may be displayed to the user including available endpoints to which the user may connect. The user may select the telepresence directly and/or select a healthcare facility or patient of interest. An optimal telepresence device may be automatically connected to if a healthcare facility or patient of interest is selected.

Figure 4:
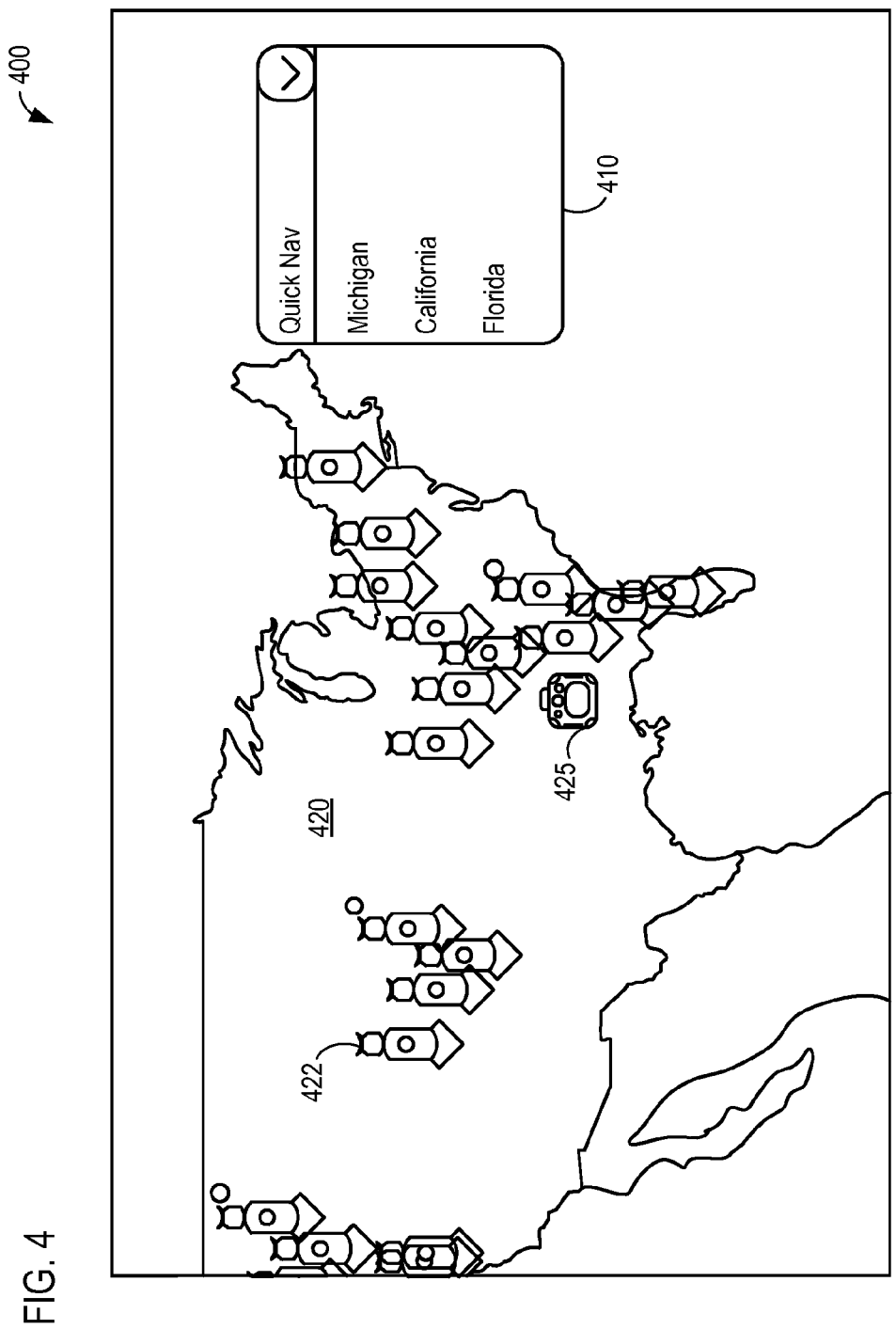
FIG. 4 is an exemplary screen display comprising a telepresence device location map.

FIG. 4 is an exemplary screen display 400 comprising a telepresence device location map 420. The locations of various telepresence devices 422, 425 may be illustrated as figures on the map 420. A Quick Nav bar 410 may allow the user to see telepresence devices available in a region of interest. The user may be able to connect to one of the telepresence devices 422, 425 by selecting the desired telepresence device from the map 420.

Figure 5:
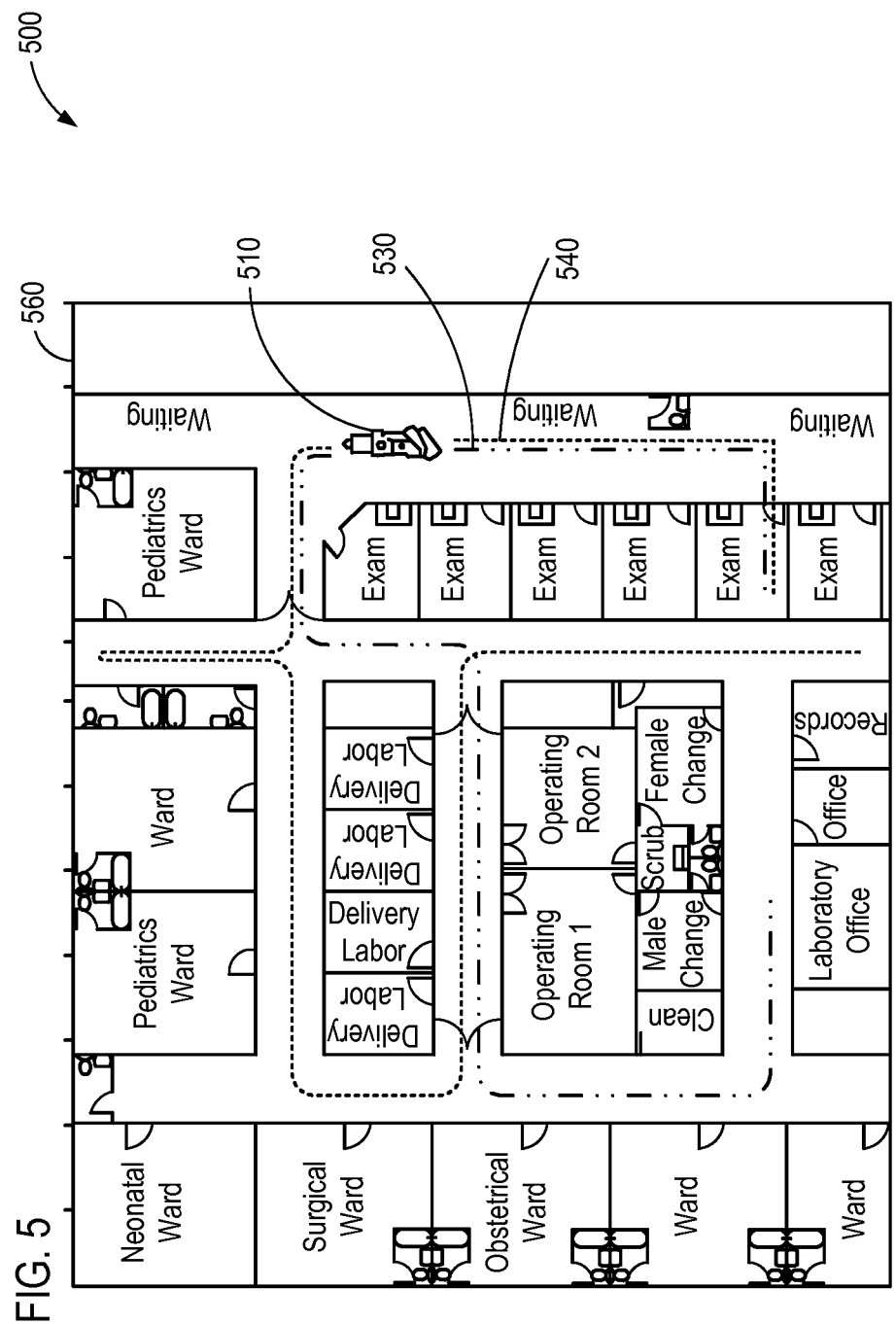
FIG. 5 is an exemplary screen display of a healthcare facility map.

FIG. 5 is an exemplary screen display 500 of a healthcare facility map 560. The healthcare facility map 560 may be displayed to the user upon initially connecting to a telepresence device 510. The user may be able to automatically and/or manually navigate the telepresence device 510 to the location of a patient of interest. The healthcare facility map 560 may indicate a previously travelled route 540 and a route 530 currently being travelled by the telepresence device 510. In some embodiments, movement of the telepresence device 510 may be controlled by a central server (e.g., the server 110).

Figure 6:
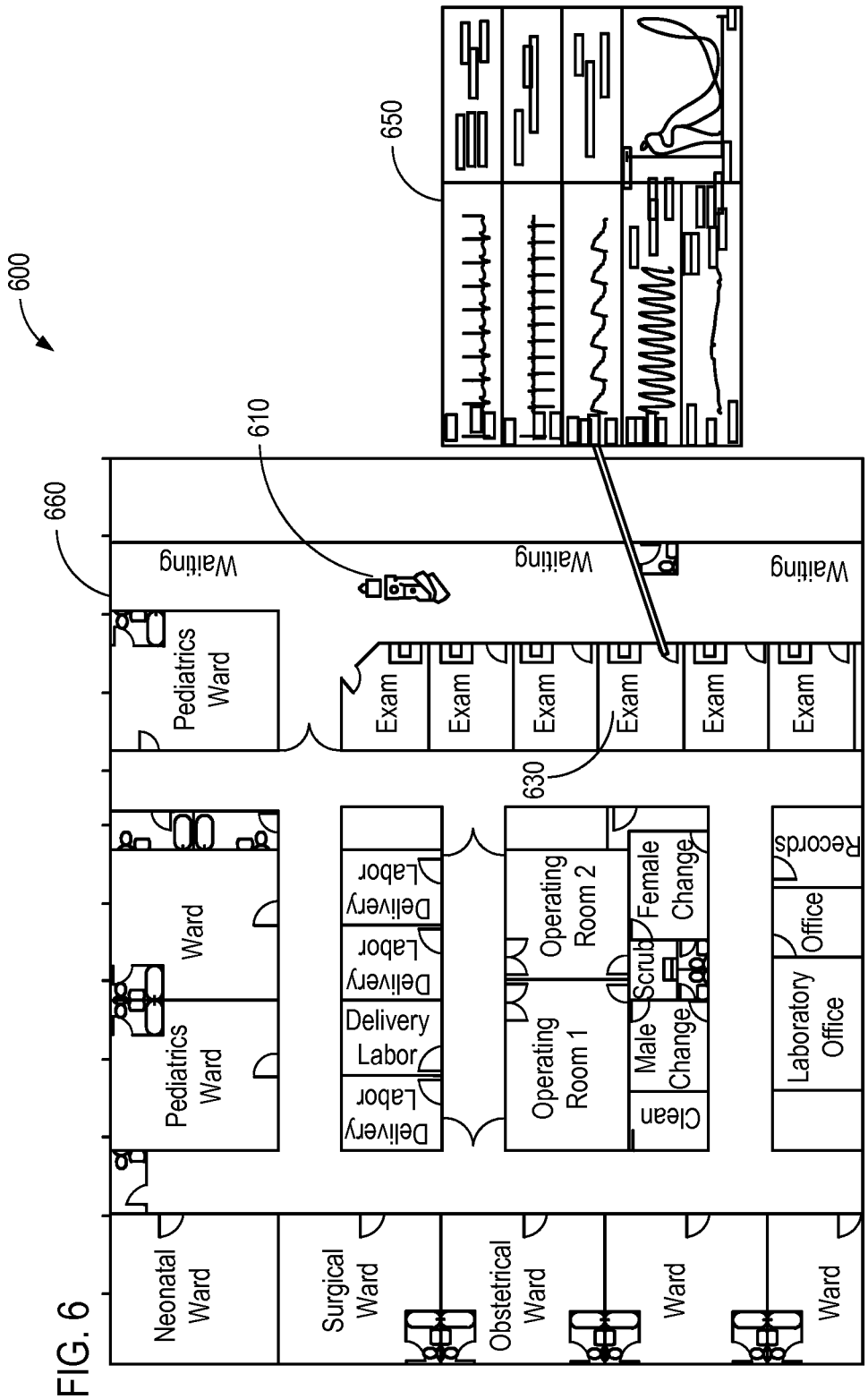
FIG. 6 is an exemplary screen display of an interactive healthcare facility map.

FIG. 6 is an exemplary screen display 600 of an interactive healthcare facility map 660. The interactive health care facility map 660 may allow a user to view patient information and/or telemetry data 650 while waiting for the telepresence device 610 to reach a destination. The telemetry data 650 may include physiological parameters displayed graphically and/or as numerical values. The user may view the patient information and/or telemetry data 650 by selecting a room 630 and/or patient of interest. In other embodiments, the user may be able to view only the patient information and/or telemetry data 650 from a patient being visited by the telepresence device or may not be permitted to see any patient information or telemetry data 650. For a patient being visited, the patient information and/or telemetry data 650 may be automatically displayed and/or manually requested by the user.

Figure 7:
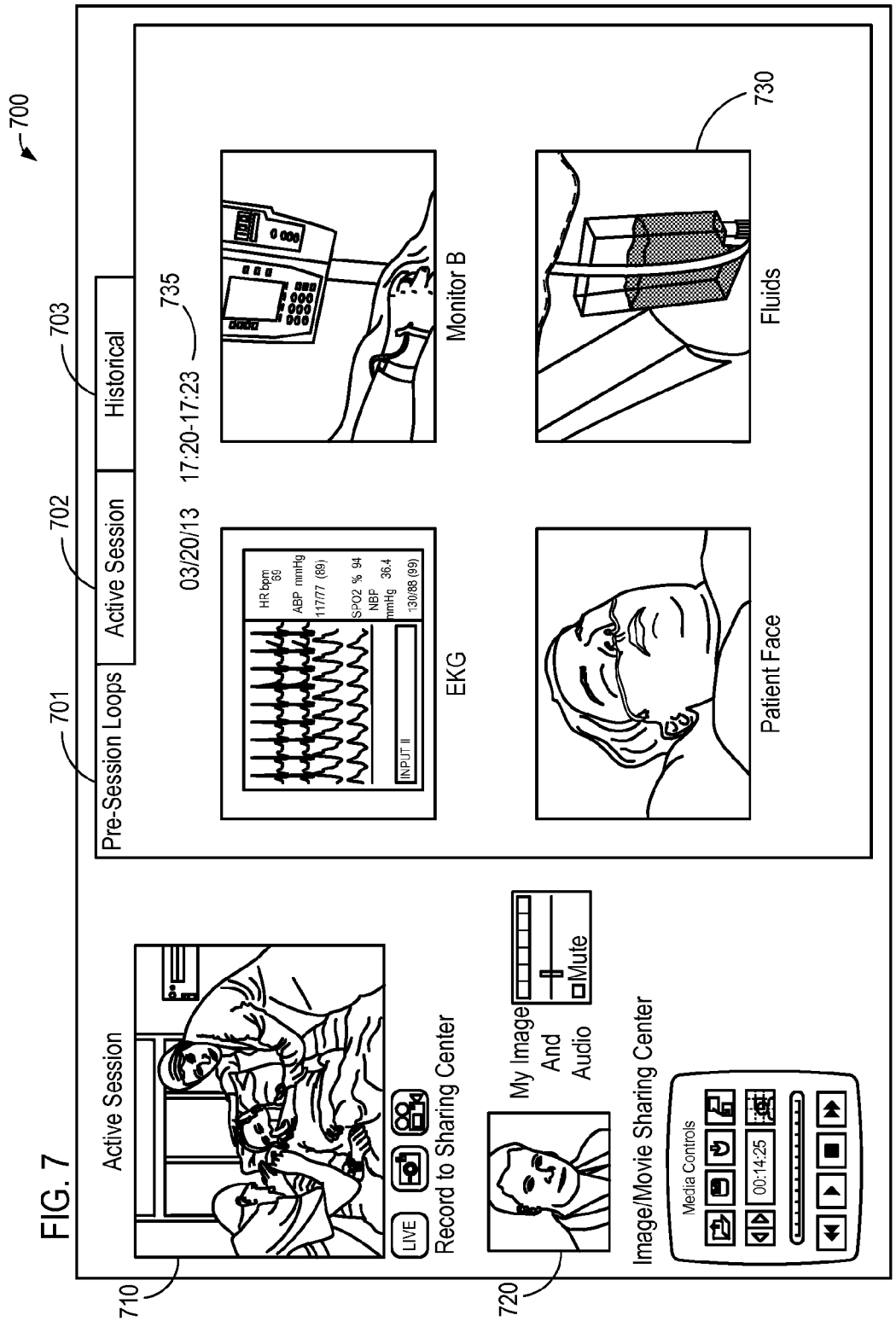
FIG. 7 is an exemplary screen display that may be seen by the user during a session with a patient.

FIG. 7 is an exemplary screen display 700 that may be seen by the user during a session with a patient. A patient device-side view 710 may show live streaming video of the patient recorded by the telepresence device. A control device-side view 720 may show video of the user captured by the control device and sent to the telepresence device for display to the patient. The control device and telepresence device may enable live, visual interaction between the patient and a medical practitioner and may allow the medical practitioner to diagnose and/or treat the patient from a remote location. A plurality of tabs 701, 702, 703 may allow the user to select between a pre-session loop interface, an active session interface, and a historical session interface, respectively.

A plurality of pre-session loops 730 may be displayed to the user when the pre-session loop tab 701 is selected. The pre-session loops 730 may include video of key elements, such as the patient's face, an EKG monitor, other monitors, a chart, fluid bags, etc., that may be of interest to a medical practitioner immediately upon connecting with the telepresence device. The pre-session loops 730 may contain important visual information that would otherwise be obtained by manually manipulating a camera to view each area of interest. Some visual information, such as facial pallor and/or fluid level/color, may not be available through standard telemetry systems. Accordingly, the pre-session loops 730 may supplement telemetry data received by the medical practitioner. In some situations, telemetry data may not be transmitted to the medical practitioners, so the pre-session loops 730 may be required to see the telemetry data as well.

The pre-session loops 730 may be generated by the telepresence device by recording short videos of areas of interest before the user connects to the telepresence device. In some embodiments, the telepresence device may be notified of which patient to visit before the medical practitioner connects. The telepresence device may receive an indication to navigate to an indicated location, such as a patient's room. The telepresence device may travel to the indicated location and face the patient's bed.

While waiting for the medical practitioner to connect, the telepresence device may scan the room by panning, tilting, and/or zooming a camera to identify the key elements. For example, the patient's face may be identified using Haar-like feature analysis, and the monitors and/or fluid bags may be identified using scale-invariant feature transform (SIFT), speeded up robust features (SURF), and/or oriented features from accelerated segment test and rotated binary robust independent elementary features (ORB). The telepresence device may zoom in on each key element thereby targeting an area of interest and record a video clip of the area of interest for a predetermined time period (e.g., five to ten seconds). If the telepresence device is still waiting for the medical practitioner to connect after video clips of each area of interest have been recorded, the telepresence device may cycle through the areas of interest again to keep the video clips as recent as possible. When the medical practitioner connects to the telepresence device, the recorded video clips may be transmitted to the medical practitioner's control device with the times when the video clips were recorded in addition to a live video feed. The time 735 and pre-session loops 730 may be displayed to the medical practitioner. The pre-session loops 730 may be repeatedly played (e.g., looped) for the medical practitioner.

Figure 8:
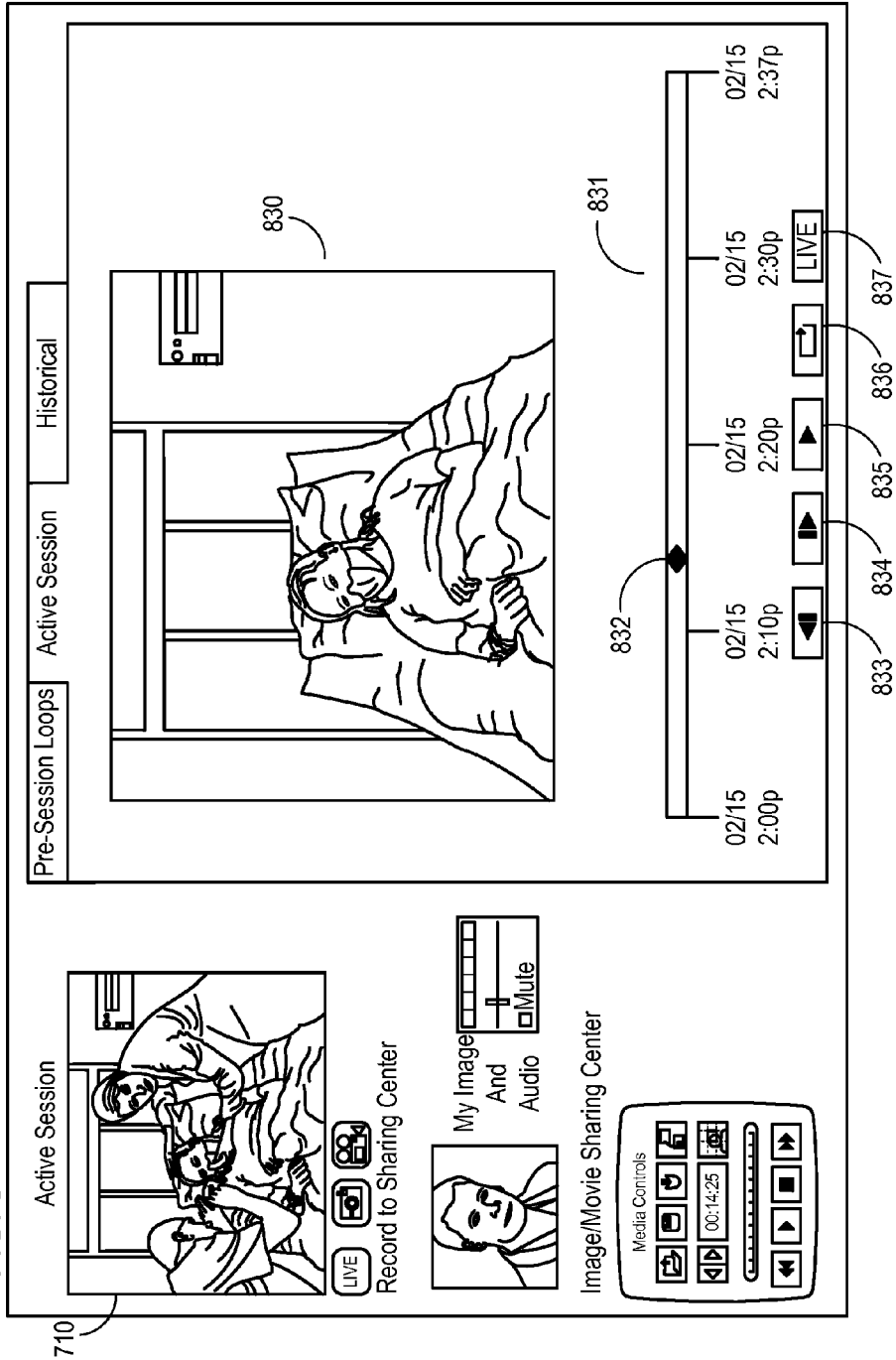
FIG. 8 is an exemplary screen display comprising one or more temporal control mechanisms.

FIG. 8 is an exemplary screen display 800 comprising one or more temporal control mechanisms 831, 832, 833, 834, 835, 836, 837. A medical practitioner may wish to quickly view historical video of a patient. For example, the medical practitioner may wish to view historical video that occurred during an active session. A timeline 831 may allow the user to select any point in a video segment recorded for the active session. The scale of the timeline 831 may change as video is recorded. The user may select a point on the timeline 831 corresponding to the time from which the user would like playback to start. In the illustrated embodiment, a diamond 832 may indicate the selected point. In an embodiment, the user may also be required to select a play button 835 before playback starts from the selected point. The play button 835 may transform to a pause button (not shown) upon selection.

A jump-to-start button 833 may allow the user to start playback at a start of the current video segment, and a jump-to-end button 834 may allow the user to start playback at an end of the current video segment. A LIVE button 837 may cause live video to start playing in an upper video window 830. In some situations, the upper video window 830 will display a larger view of the patient device-side view 710. However, if media, such as an educational video, is being shared with the patient, the patient device-side view 710 may show the educational video rather than the patient. A loop button 836 may allow a section of video to be looped.

Figure 9:
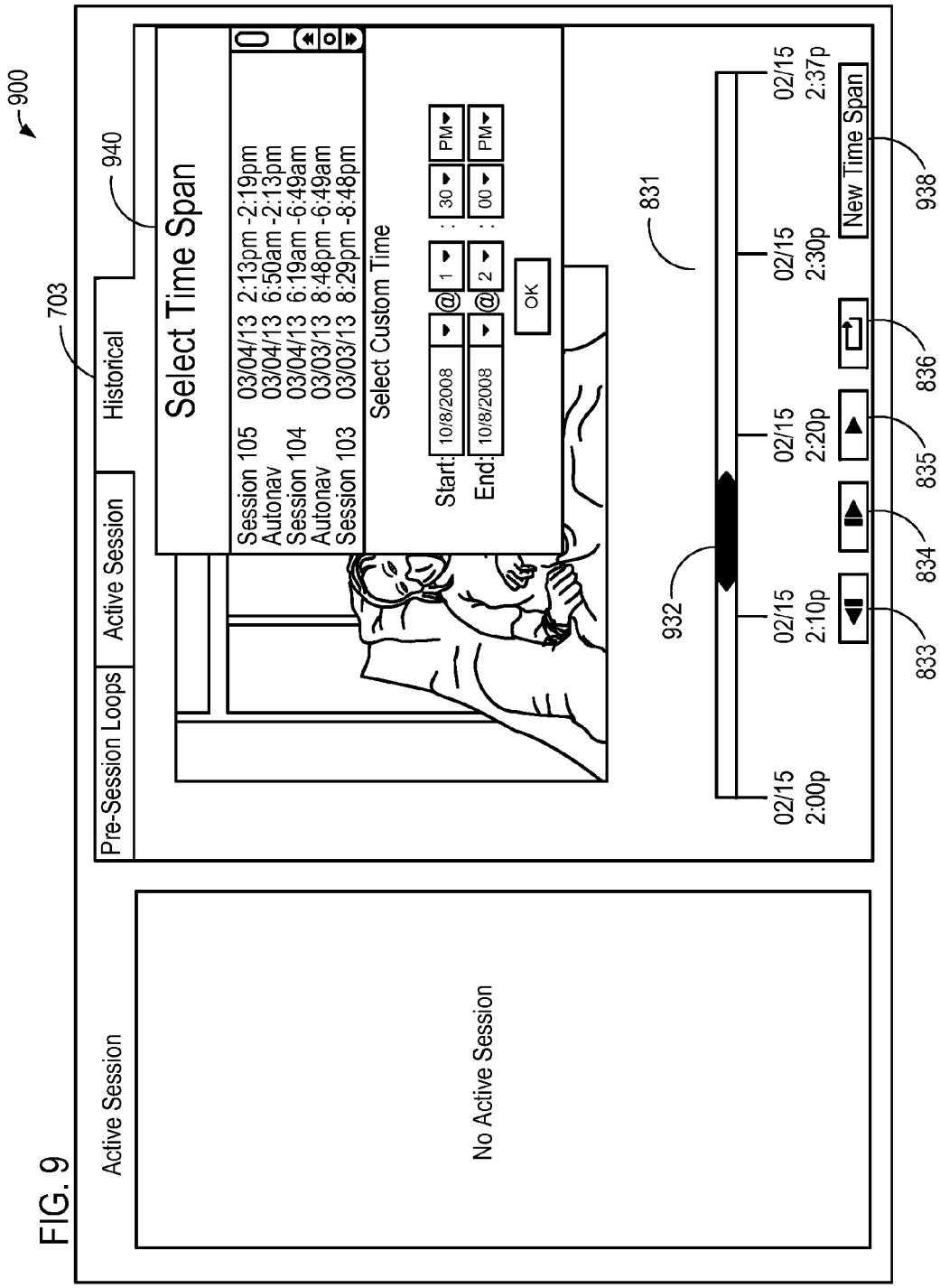
FIG. 9 is an exemplary screen display comprising one or more temporal control mechanisms for historical video segments.

FIG. 9 is an exemplary screen display 900 comprising one or more temporal control mechanisms 831, 932, 833, 834, 835, 836 for historical video segments. The historical video segment may have been recorded during a previous telepresence session, during local caregiver use of the telepresence device, and/or during autonomous off-line activities of the telepresence device. Video streamed from the telepresence device may be broken up into video segments. For example, the streamed video may be broken up based on sessions and time spent autonomously navigating off-line. When the user selects the historical tab 703, a select time span box 940 may prompt the user to select a video segment. The user may also be to select custom time spans by selecting a new time span button 938. The new time span may not wholly correspond to the existing time spans. Instead, it may be larger or smaller than the existing time spans and/or overlap with multiple existing time spans. The user may be able to interact with a new video segment corresponding to the new time span.

During either the active or the historical viewing, the user may be able to click and drag on the timeline 831 to select a span of time. In the illustrated embodiment, the span of time may be indicated by an elongated diamond 932. The user may select play button 835 or the play loop button 836 to play the selected span of time once or repeatedly, respectively. In some embodiments, the play loop button 836 may be disabled unless a span of time is selected. Looped video may be helpful, for example, when a medical practitioner is trying to review and analyze video of an EKG monitor.

Figure 10:
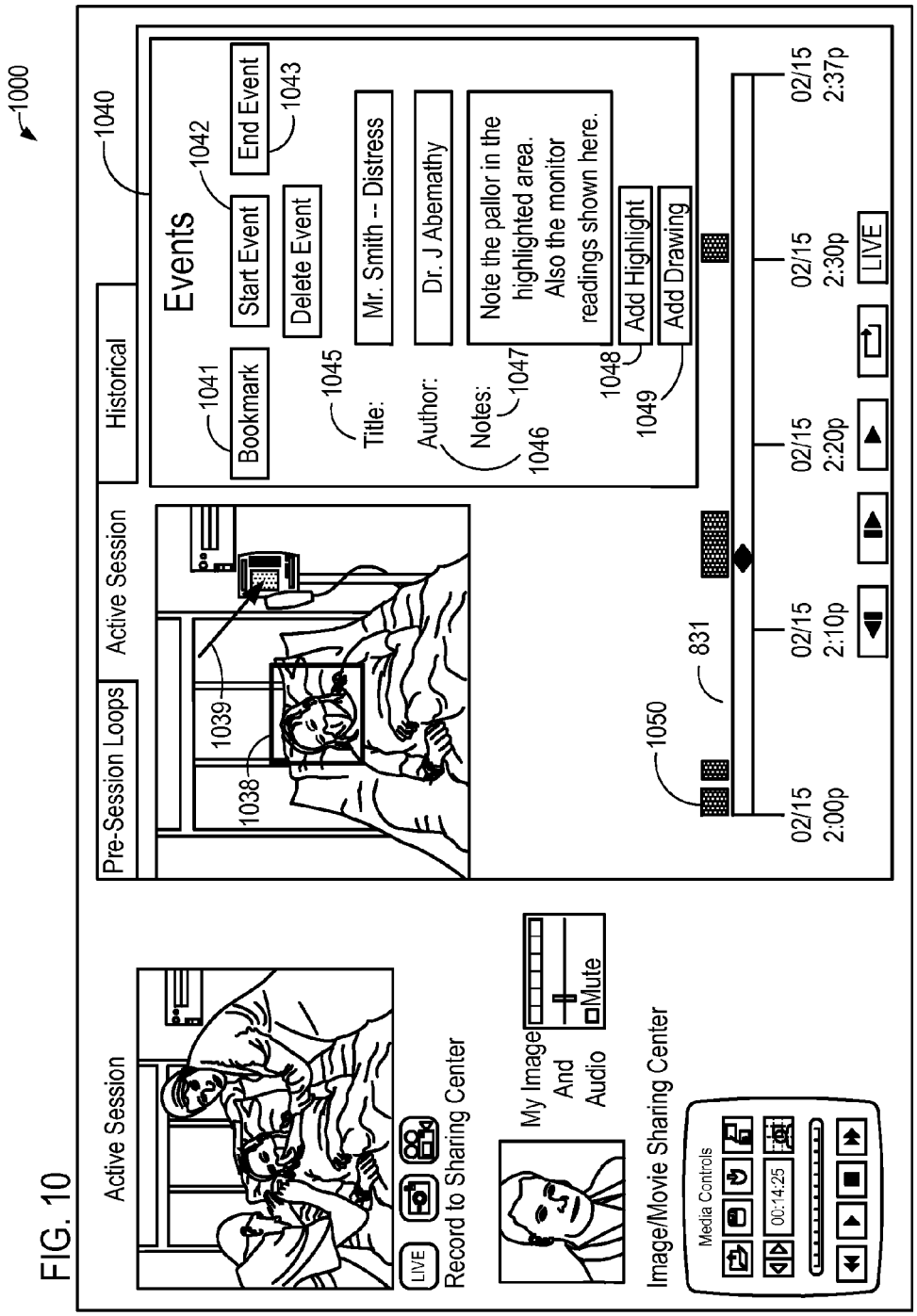
FIG. 10 is an exemplary screen display with an event added to a video segment.

FIG. 10 is an exemplary screen display 1000 with an event 1040 added to a video segment. The event 1040 may be added to the video segment by a user live during a session and/or during historical playback. The event 1040 may be an annotation, such as text, a drawing, a marking, etc. Annotations may be overlaid on the video segment. Other users may be able to add notes to an annotation after creation, and an indication of who added each note may be saved. The user may be able to add the event 1040 by selecting a start event button 1042 or a bookmark button 1041. The user may select the time span for the event 1040 by selecting an end event button 1043 at a time in the video when the event 1040 should end. For bookmarks, a default length of time may be used to determine when the event 1040 ends.

The user may be able to input a title 1045 and notes 1047 for the event as text. An add highlight button 1048 may allow the user to draw a box 1038 over the video, and an add drawing button 1049 may enable a drawing function when the cursor is over the video (e.g., allowing user to draw an arrow 1039). The drawings and/or highlighting may be visible only when the time span of the event. Similarly, the title and/or notes may be associated in memory with the time span, so they are only displayed during the time span and/or so it can be indicated to the user that they are associated with that time span. In an embodiment, the author 1046 for the event is automatically completed with the user's name. The author 1046 may be the original creator of the event 1040. Notes, drawings, and highlighting from other staff may be separately tagged to indicate who added them.

In an embodiment, rectangles 1050 with rounded edges may indicate events. The rectangles 1050 may be located just above the timeline 831 and the length of each rectangle may correspond to the time span of each event. A user may be able to select a rectangle 1050 to view the corresponding event. Hovering over the rectangle 1050 may cause a balloon or callout to display the title, if any, of the corresponding event. In other embodiments, various interactive indications may be used to alert the user to saved events.

Figure 11:
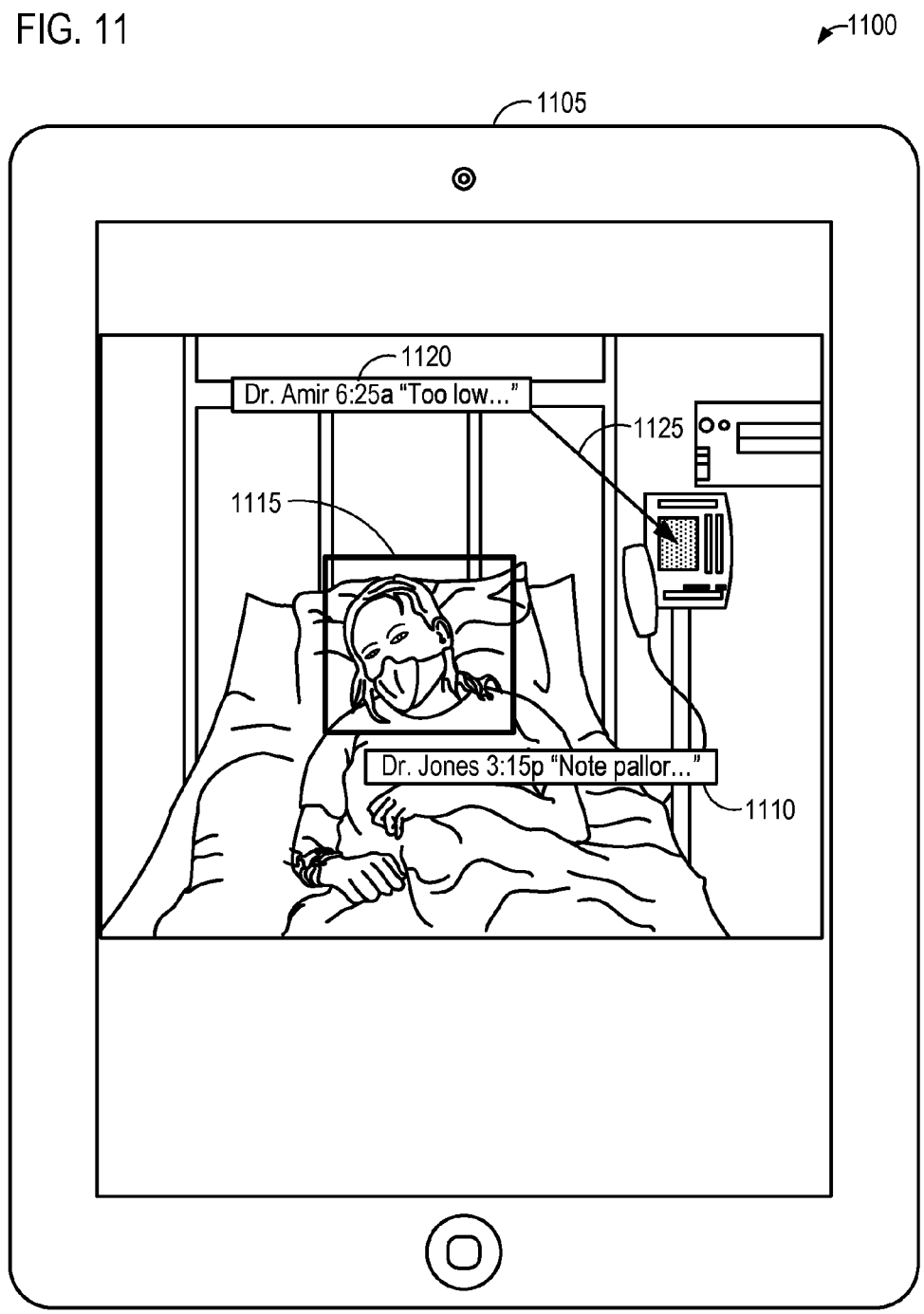
FIG. 11 is an exemplary screen display on a control device during recall of notes, drawings, and/or highlights made during a predetermined time period.

FIG. 11 is an exemplary screen display 1100 on a control device 1105 during recall of notes 1110, 1120, drawings 1125, and/or highlights 1115. A second healthcare practitioner may wish to see all notes 1110, 1120, drawings 1125, and/or highlights 1115. The second healthcare practitioner may view live video of a patient filmed using a rear camera (not shown) of the control device 1105, and the notes 1110, 1120, drawings 1125, and/or highlights 1115 for the patient may be automatically displayed on the video. Authors and timestamps for each note 1110, 1120, drawing 1125, and/or highlight 1115 may be displayed. In an embodiment, the second healthcare practitioner may specify that annotations from only certain authors and/or with timestamps in a predetermined range should be viewed.

In an embodiment, when an event is created by a first user, first location data for video to which the event was added may be stored. For example, the room number where the video was taken, the position and/or orientation of the telepresence device, the pan, tilt, and/or zoom of a camera, and/or a set of image descriptors used for pattern matching (e.g., from SIFT, SURF, ORB, or the like) may be saved as the first location data. Position and/or orientation data may be extracted from the navigation system of the telepresence device, and pan, tilt, and/or zoom information may be extracted from encoders in the camera or head of the telepresence device. In an embodiment, the first location data may correspond to the location being viewed rather than the location from which images and/or video were recorded. For example, the annotation may be associated with a specific object within an image and the first location data may describe the location of the object.

The second user may input general location or position information, such as a room number, to narrow searching and point the rear camera of the control device 1105 at a desired area to capture a picture and/or video. Second location data may be generated from pattern matching of an image, such as a video frame, captured by rear camera and/or from the user-selected room number. Scale-invariant feature matching of the image may determine whether the first and second location data are within the predetermined threshold. If the second location data is within a predetermined threshold of the first location data, the notes 1110, 1120, drawings 1125, and highlights 1115 or an abbreviated form thereof (e.g., a preview) may be displayed.

Alternatively, or in addition, when using a telepresence device with a robotic platform/base, for example, inverse kinematics may be used to match a current position/orientation/pan/tilt/zoom image framing with the image framing when an annotation and associated position, orientation, pan, tilt, and/or zoom data were stored. In an embodiment, both scale-invariant pattern matching and inverse kinematics may be used for increased robustness. While the results of each algorithm may be noisy, the system may utilize Kalman filtering on the redundant data streams to determine most likely positions.

Figure 12:
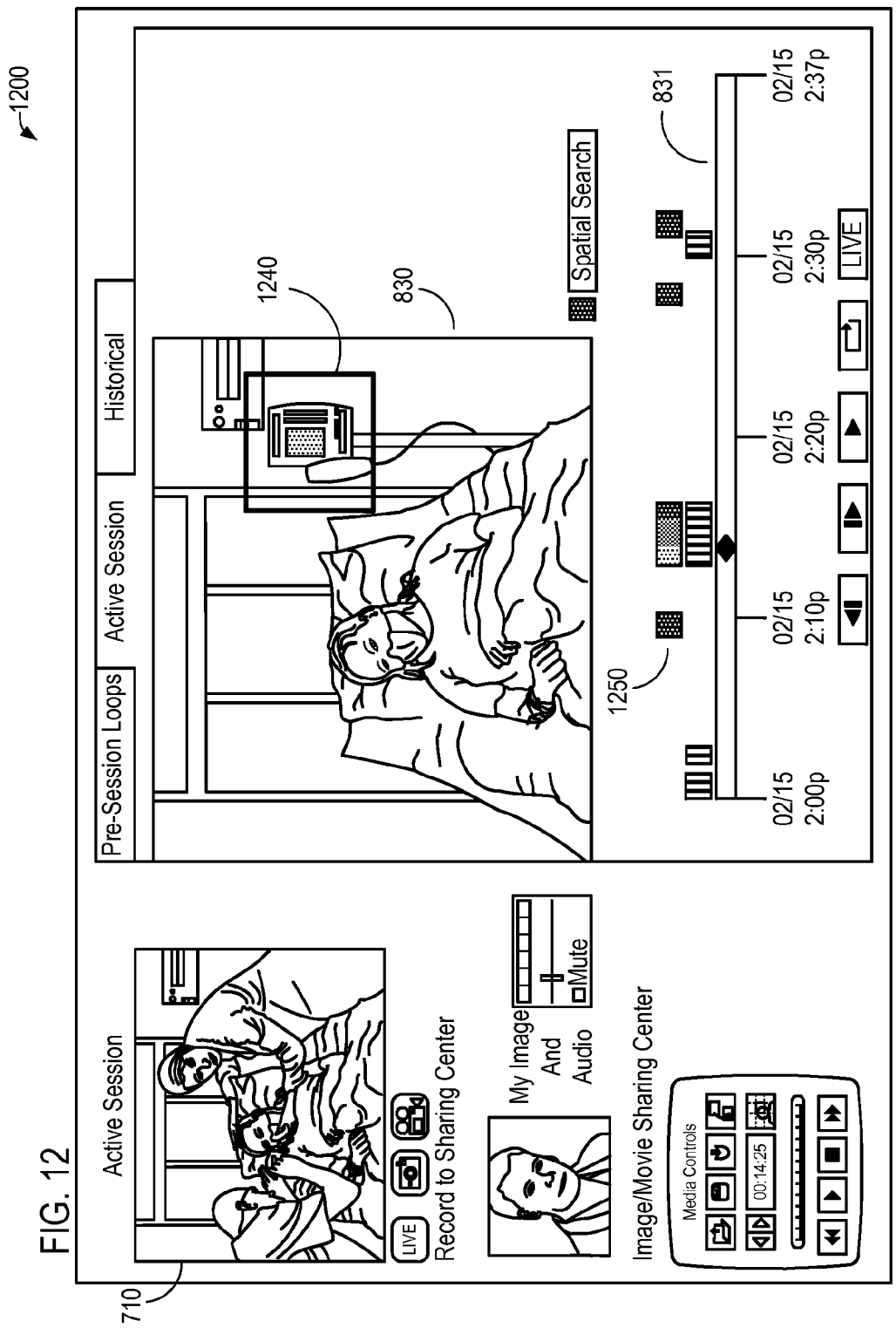
FIG. 12 is an exemplary screen display showing spatial searching of a video segment.

FIG. 12 is an exemplary screen display 1200 showing spatial searching of a video segment. A user may wish to search a video for an object contained in a frame of the video to determine when in the video that object appears. For example, a medical practitioner may want to view all footage of a patient monitor, fluid bag, or body part of the patient to see how the readings, fluid color, or patient pallor has changed over time. The user may be able to draw a box 1240 around an area of interest in a video frame while the video is paused. Inverse kinematics and/or pattern matching from image descriptors may be used to identifying portions of the video correlated with the area of interest.

A layer 1250 above the timeline 831, for example, may indicate matches. The layer 1250 may comprise a plurality of rectangles corresponding to each time the area of interest appeared. The layer 1250 may indicate ratings for each match based on the relative size of the area of interest in each match. In an embodiment, the rating may correspond to a color brightness at each location in the layer 1250 with a brighter color indicating a larger size in the match. In a configuration, the user may review the matches in the upper video window 830 while watching the area of interest live in the patient device-side view 710.

In an exemplary use, a healthcare practitioner may review a video of a surgery to determine what occurred at a certain spot on the patient. In another exemplary application, a healthcare practitioner may believe a patient's EKG has changed recently but is unsure. A spatial search on the EKG may indicate previous time spans when a camera was recording the EKG. In an industrial example, a telepresence device may have inspected various objects in a remote scene over a protracted time period. A user may wish to examine a close-up image of a counterbalance reel but does not want to search video for the entire protracted time period. The user can draw a box around the counterbalance reel, and the system may find the relevant portions of the video.

Figure 13:
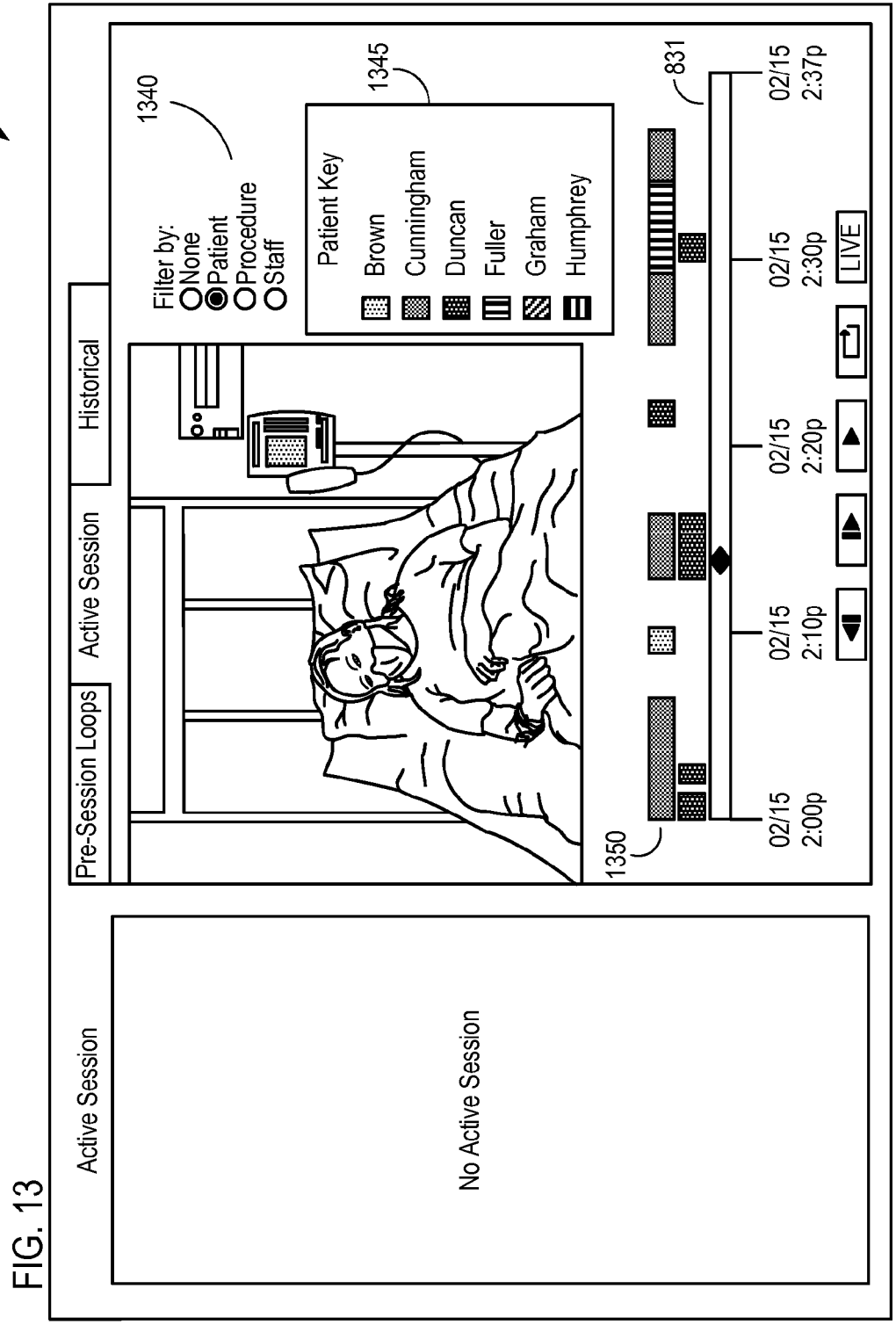
FIG. 13 is an exemplary screen display of results from a contextual search.

FIG. 13 is an exemplary screen display 1300 of results 1350 from a contextual search. Various situational data may be identified by the telepresence device and stored with recorded video. The situational data may include a room number, patient name, patient complaint, procedure being performed, healthcare practitioner operating the telepresence device, and the like. The situational data can be used to search the recorded video for video segments matching a situation of interest. For example, a reviewing healthcare professional may wish to see all past video of a patient; stored videos of certain procedures may be used for training; and/or videos where a particular healthcare professional was operating the telepresence devices may be used to provide feedback. In an embodiment, the telepresence device may know the room number for a video segment but not the patient name or procedure. A healthcare practitioner may input a procedure being performed and/or a patient name and a corresponding room number for the procedure or patient name. The input may be used to map the room number to the patient name or procedure.

A filter criterion 1340 may be used to identify video segments according to situational data elements corresponding to the filter criterion 1340. For example, a healthcare practitioner may specify a filter criterion 1340 of patient, and the video segments may be identified by patient name. In an embodiment, a key 1345 may specify a color corresponding to each unique situational data element. The results 1350 may comprise a layer above the timeline 831 including one or more rectangles containing colors from the key 1345. In an embodiment, hovering over any of the one or more rectangles in the results 1350 may cause a balloon or callout text to display the value of the situational data element.

A telepresence device may be configured to provide synchronized location and video replay. For a mobile telepresence device, such as a telepresence device with a robotic base, a local or remote user may desire for the telepresence device to retrace a previous route and play back video recorded while traversing that route. For example, a healthcare practitioner may have missed group rounds and wish to visit each patient via the telepresence device while seeing what occurred during group rounds. In such an example, the telepresence device may have been configured to follow a group of people during group rounds without a remote user controlling the telepresence device. During the autonomous following, the telepresence robot may actively record both a video stream from the camera and position and orientation data from the navigation system, synchronized with the video stream. In an embodiment, a trace route button (not shown) may be available during playback of a recorded video. In response to the trace route button being selected, the telepresence device may access stored position and/or orientation data to determine a location and/or route corresponding to the video being played back.

In an embodiment, the video may be paused with a message "Driving to video position" overlaid on the video while the telepresence device navigates to the location corresponding to a current playback position in the video. When the telepresence device arrives at the location, video playback may resume and/or the telepresence device may begin retracing the route corresponding to the video. The user may be able to pause the video, which may also pause movement of the telepresence device. While the video is paused, the user may control the telepresence device and interact using live video with, for example, other healthcare practitioners and/or patients. When the user presses play, the telepresence device may automatically return to the position where it was paused and continue playback and corresponding navigation. The user may be able to add notes, drawings, and/or highlights to the recorded video.

The telepresence device may be configured to attempt to stay within a first predetermined distance of the location and/or route corresponding to the current playback position in the video (e.g., the position during original recording). If the telepresence device is more than the first predetermined distance from the location and/or route, the video may be paused and a message "Catching up to video position" may be overlaid on the video. Once the telepresence device is within a second predetermined distance of the location and/or route, playback may resume. The second predetermined distance may be smaller than the first predetermined distance to create a hysteresis loop. For example, playback may stop when the telepresence device is more than ten feet from the desired position and resume when the telepresence device returns to less than five feet from the desired position.

Figure 14:
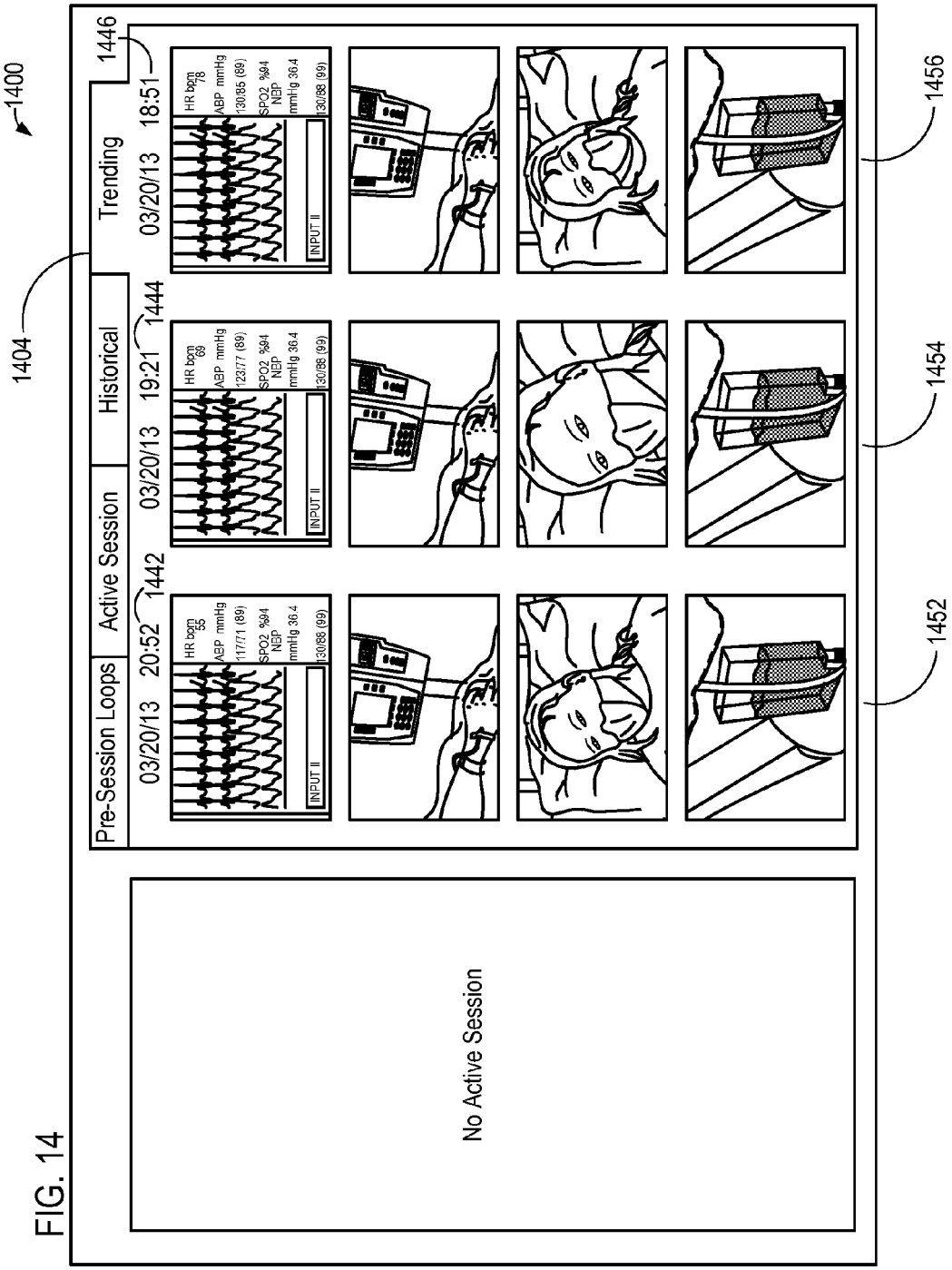
FIG. 14 is an exemplary screen display a series of stored trend videos for a plurality of areas of interest.

FIG. 14 is an exemplary screen display 1400 of a series of stored trend videos 1452, 1454, 1456 for a plurality of areas of interest. Diagnoses and/or treatment of a patient by a healthcare practitioner may be improved comparing imagery over time. For example, the healthcare practitioner may look for changes in the pallor, fluid color or level, and/or various monitors attached to the patient.

In an embodiment, the telepresence device may be configured to autonomously visit a plurality of patients on a predefined schedule. For each patient, the telepresence device may scan the room for pre-defined areas of interest using, for example, a built-in camera. For example, the telepresence may attempt to recognize the patient's face, one or more monitors, fluid bags, and the like using Haar-like feature matching, SIFT, SURF, ORB, and/or the like. For each area of interest identified, the telepresence device may zoom a camera on the area of interest and record video for a predetermined time period (e.g., ten seconds). The recorded video may be stored by the telepresence device and/or a server. A corresponding time stamp may also be stored with the recorded video. The telepresence device may proceed to the next patient's room after the video has been recorded.

A control device may load and display a series of stored trend videos 1452, 1454, 1456 when the user selects a trending tab 1404. Each video may play for the predetermined time period automatically and/or after manual selection. A corresponding time stamp 1442, 1444, 1446 may be displayed for each set of videos 1452, 1454, 1456 in the series to inform the user when the video was recorded. In an embodiment, the user may be able to enlarge a video to full size by double-clicking on it.

Figure 15A:
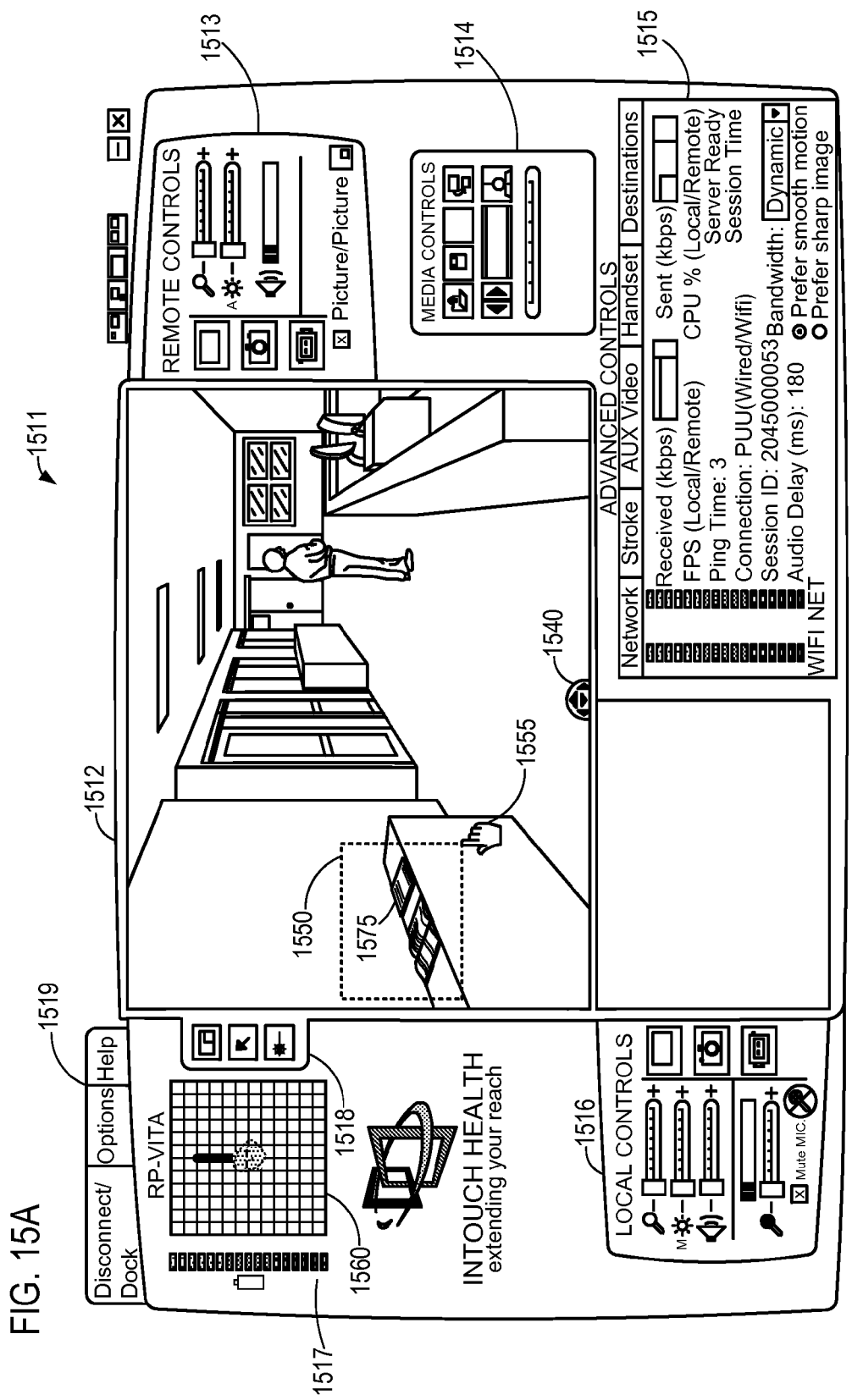
FIG. 15A illustrates a box drawn within a video feed to zoom/magnify a portion of the video feed.

FIG. 15A illustrates a control device 1511 with a box 1550 drawn within a video feed 1512 to zoom in on a portion of the video feed 1512. As illustrated in FIG. 15A, the control device 1511 may include a four way controller 1540 selectively overlaid on the live video feed 1512. Various additional panels, icons, tabs, and/or other objects 1513, 1514, 1515, 1516, 1517, 1518, and 1519 may be selectively displayed. Any of a wide variety of functional icons, buttons, drive modes, maps, and/or other panels, windows, and/or objects described herein may be displayed or selectively displayed in conjunction with the zoom box 1550 functionality.

An operator may indicate a desired zoom region by creating a box 1550 around a portion of the video feed 1512. Alternatively or additionally, an operator may simply click a center of a desired region, define a region using a touch input, define a region using a cursor 1555, and/or otherwise select a portion of the video feed 1512. In the illustrated embodiment, the portion selected includes printed materials containing informational content. A zoom function of any type, including the illustrated box zoom 1550, may be used to zoom in on any portion of the video feed 1512.

Figure 15B:
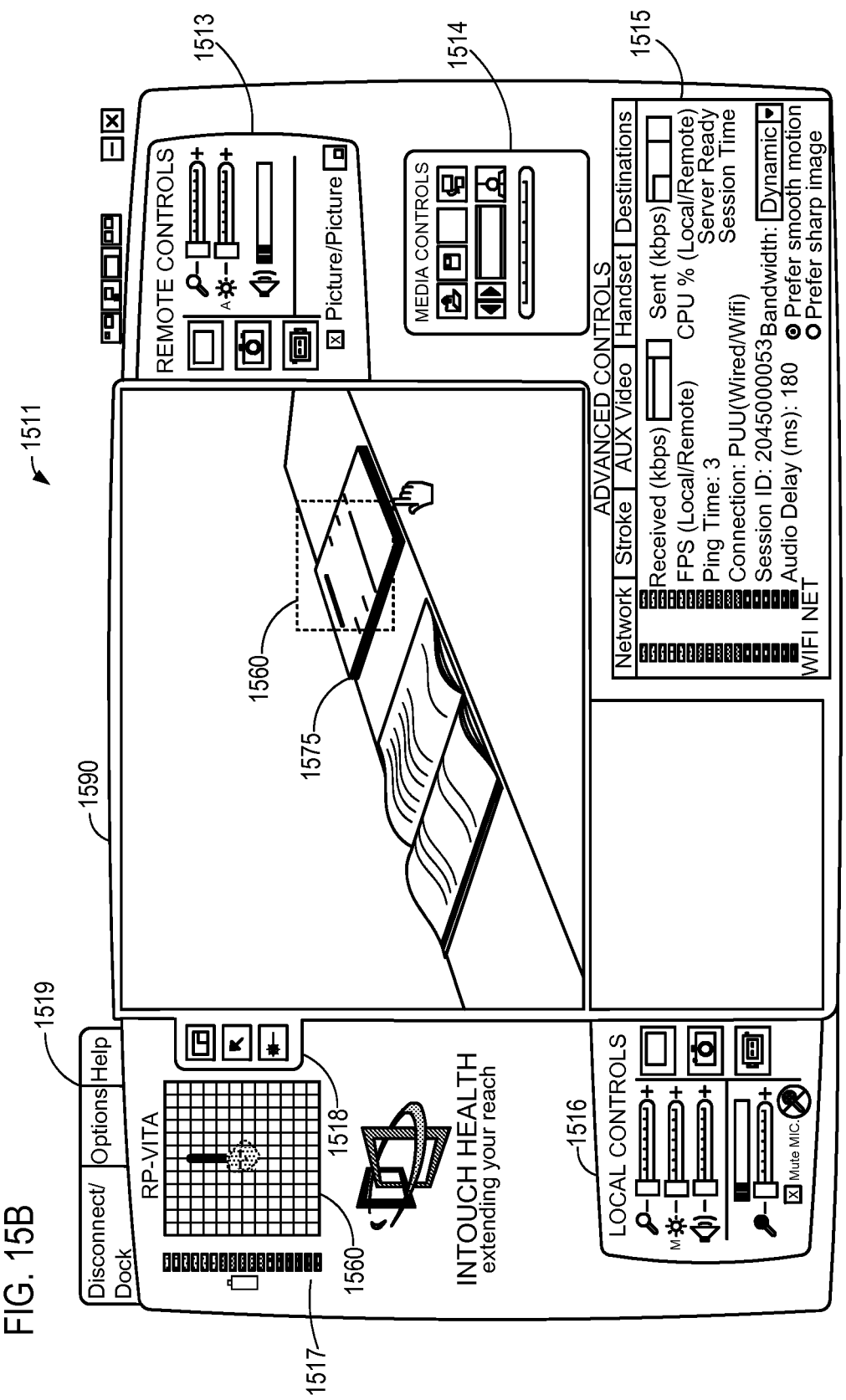
FIG. 15B illustrates a zoomed view of the video feed with a second box drawn for additional zooming on a document.

FIG. 15B illustrates a zoomed view 1590 of the video feed 1512 (FIG. 15A) with a second box 1560 drawn for additional zooming on a document 1575. A zoom request may be generated using any of a wide variety of selection methods for selecting a portion of the zoomed view video feed 1590. In the illustrated embodiment, a zoom request is made by defining another box 1560. A zoom request may cause the selected portion of the video feed 1590 to be magnified. Magnifying the video feed may be performed in any number of ways, including transmitting instructions to adjust an optical zoom of a camera of the telepresence device, digitally zooming the selected portion 1560 of the video feed 1590 and/or transmitting navigation instructions to the telepresence device to cause the telepresence device to navigate in the direction of the selected portion 1560 of the video feed 1590.

Figure 15C:
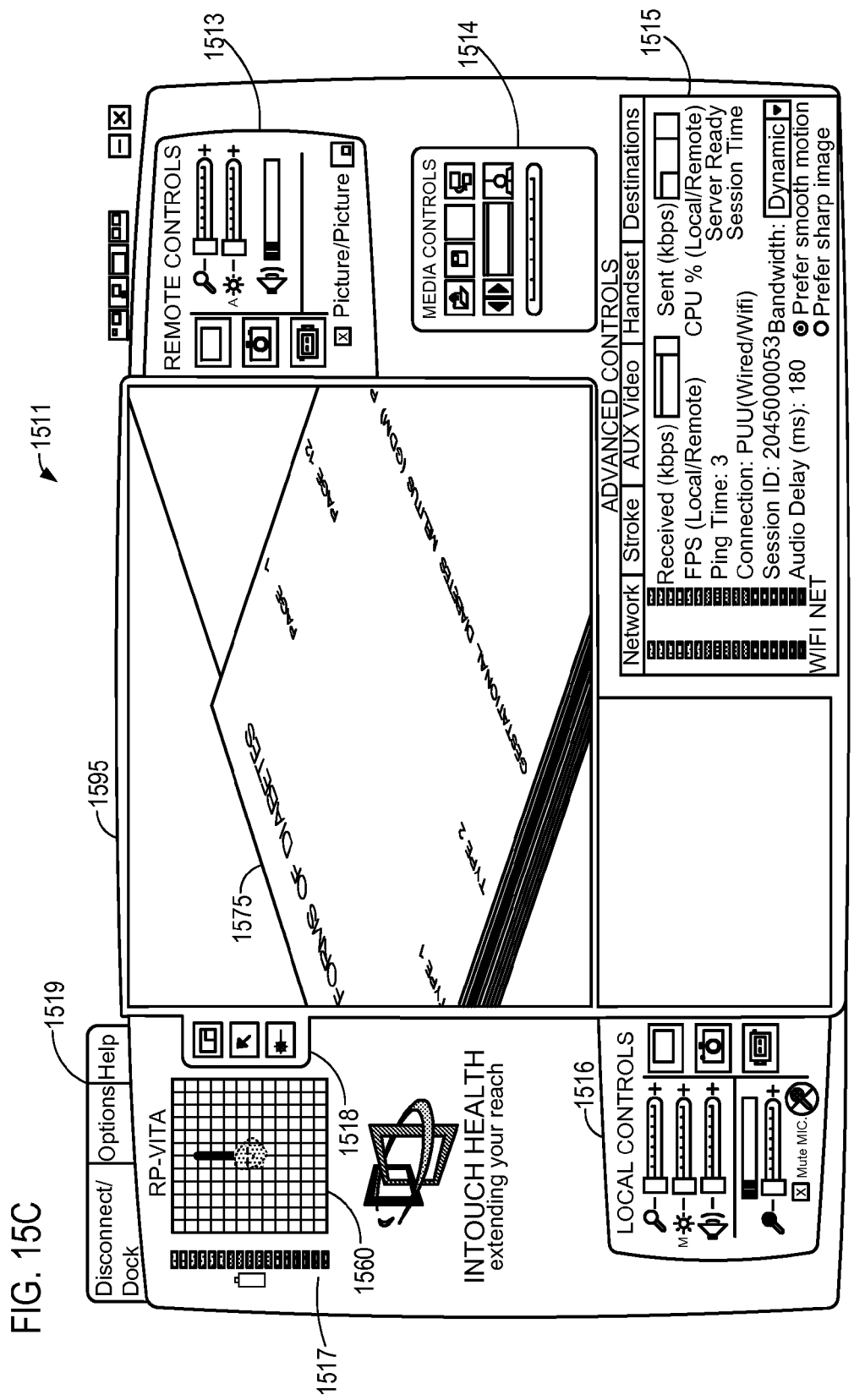
FIG. 15C illustrates a zoomed view of the document with the text at an angle and skewed.

FIG. 15C illustrates a zoomed view 1595 of the document 1575. The text of the document 1575 may not be perfectly aligned with the camera of the telepresence device. Accordingly, the text, images, charts, etc. of a document or other information content may be misaligned with respect to the orientation of the video feed. For example, the text, images, charts, etc. may be at an angle relative to the video feed 1585 and/or skewed due to the relative angle of the informational content. According to various embodiments, the control device 1511 may be configured to automatically align the informational content within a video feed 1512, 1590, and 1595.

Initially, objects that potentially have information content of interest may be identified, such as telemetry monitors, hospital signs, patient charts, lab results on a nursing station, room numbers, or the like. Objects of interest may be identified by automatically recognizing shapes that correspond to objects of interest. Uninteresting objects may share similarities with objects of interest, so color, shape, position, and/or user preferences may be used to learn to differentiate objects of interest from uninteresting objects. Alternatively, or in addition, objects of interest may be identified using trained SIFT features. Detected objects of interest may be leveraged for other purposes, such as to assist navigation and/or automatically create waypoints (e.g., during map generation). For example, room numbers and/or wall paintings may be recognized for navigation and/or to build waypoints. Room numbers may be used to automatically create waypoints and a corresponding structured list of user-available waypoints.

In an embodiment, potential objects of interest may be highlighted and/or outlined in the received video, and the user may select an object for alignment. Alternatively, or in addition, the telepresence device, server, and/or control device may automatically determine whether or not an object should be aligned. In some embodiments, the informational content may not be automatically aligned unless the information content comprises a sufficient portion of the displayed content within a video feed 1512, 1590, and 1595. Alternatively, the informational content may be automatically aligned only if it would be legible within the video feed 1512, 1590, and 1595. For example, in FIG. 15A, the information content (the document 1575) may not comprise a sufficient portion of the video feed 1512 to be automatically aligned, while the same document 1575 in the zoomed view 1595 of FIG. 15C would be automatically aligned. To align the information content, the system may identify the four salient edges of the object using, for example, Hough line detection, and thereby identify the corners of the information content. Once the corners are identified, the system may automatically rotate and/or deskew the image of the object for display. In an embodiment, the identified corners may be mapped to predetermined and/or corresponding aligned locations, such as the corners of a rectangle, and the area inside the corners may be correspondingly adjusted. The user may be able to resize the length, width, and/or both for the deskewed image. Alternatively, or in addition, information content may be converted to text, such as using optical character recognition (OCR).

In an alternative embodiment, the document 1575 (or other information content, such as an electronic display or patient monitor) may not be automatically aligned. Rather, the information content may be selectively (though automatically) aligned based on a user selection and/or be manually aligned through one or more manual alignment tools (e.g., a rotate function, a deskew function, and/or a function allowing the user to identify corners of the information content).

Alternatively, or in addition, the position and/or orientation of the telepresence device may be modified relative to the information content. The telepresence device may be brought directly in line with the information content to align the information content. A position of the information content may be computed using pixel mapping and/or the pan, tilt, and/or zoom of the camera. The information content position may be projected onto a two dimensional plane parallel to or coincident with the floor. The orientation of the information content may be determined (e.g., using OCR), and a line and/or ray in the two dimensional plane corresponding to the orientation and intersecting the projected information content position may be computed. The points of the line may be lined up positions to which the robot may move to view aligned information content (e.g., the two dimensional plane may correspond to possible positions to which the telepresence device can navigate, and the line may correspond to points where the information content may be aligned when viewed). The telepresence device may be directed (and/or may decide) to navigate to the closest unobstructed point and/or the closest unobstructed point exceeding a minimum distance. The line and/or two dimensional plane may also be used to orient the telepresence device directly towards the information content once the telepresence device has navigated to the desired location.

FIG. 15D illustrates a zoomed view 1597 of the document 1575 with the text deskewed and rotated. Comparing FIGS. 15C and 15D, it is apparent that the digitally aligned text in FIG. 15D is easier to read than the actual (misaligned) zoomed view 1595 of the document 1575 in FIG. 15C. In various embodiments, the informational content may comprise documents, charts, images, text, and/or other informational material. The information content may be physically displayed and/or electronically displayed. In some embodiments, the informational content may be further enhanced, such as, for example, by adjusting the contrast of the informational content.

In some embodiments, informational content displayed on an electronic display captured by a camera of a telepresence device and displayed by the control device may have various video artifacts, such as scrolling bars or darker sections due to unsynchronized refresh rates. Accordingly, the control device 1511 may automatically synchronize refresh rates and/or otherwise compensate for unsynchronized refresh rates in order to improve the display of electronically displayed informational content.

According to various embodiments, a telepresence and/or control device may be configured with all or some of the features and embodiments described herein. For example, a telepresence and/or control device may include any number of the features and embodiments described herein as selectively displayed and/or selectively functional options. An explicit enumeration of all possible permutations of the various embodiments is not included herein; however, it will be apparent to one of skill in the art that any of the variously described embodiments may be selectively utilized, if not at the same time, in a single telepresence and/or control device.

It will be understood by those having skill in the art that many changes may be made to the details of the above-described embodiments without departing from the underlying principles of the disclosure. The scope of the present disclosure should, therefore, be determined only by the following claims.

The invention claimed is:

1. A non-transitory computer-readable storage medium including computer-readable instruction code for performing a method of generating pre-session video loops, the method comprising:
   receiving, at a telepresence device, an indication to navigate to an indicated location;
   adjusting a camera on the telepresence device to identify one or more areas of interest at the indicated location;
   sequentially targeting each area of interest with the camera;
   recording video of each area of interest for a predetermined time period; and
   transmitting the recorded video to a remotely located control device, wherein the one or more areas of interest contain an object selected from the group consisting of a patient's face, an EKG monitor, a chart, and a fluid bag.

2. The non-transitory computer-readable storage medium of claim 1, wherein recording video of each area of interest comprises continuously cycling through the one or more areas of interest until receiving a connection request from the remotely located control device.

3. The non-transitory computer-readable storage medium of claim 1, wherein the method further comprises recording a time.

4. A non-transitory computer-readable storage medium including computer-readable instruction code for performing a method of providing segmented temporal video control of video received from a telepresence device, the method comprising:
receiving streaming video from the telepresence device;
determining a plurality of video segments corresponding to a plurality of telepresence device activities;
displaying a first video segment associated with a first telepresence device activity to a user;
providing a temporal control mechanism to the user permitting the user to select a first playback point within the first video segment;
receiving an indication of a desired time span from the user, wherein none of the plurality of determined video segments wholly correspond to the desired time span;
determining a desired video segment corresponding to the desired time span; and
displaying the desired video segment to the user.

5. The non-transitory computer-readable storage medium of claim 4, wherein the method further comprises receiving an indication of a desired video segment from the user.

6. The non-transitory computer-readable storage medium of claim 5, wherein the method further comprises receiving an indication from the user to play the desired video segment in a loop.

7. A non-transitory computer-readable storage medium including computer-readable instruction code for performing a method of annotating video segments received from a telepresence device, the method comprising:
receiving streaming video from the telepresence device;
displaying a video segment from the streaming video to a user;
receiving an indication of a desired time span from the user;
receiving an annotation corresponding to the desired time span from the user;
storing the received annotation in association with the desired time span; and
displaying an interactive indication in a location corresponding to the desired time span, wherein the user may access the received annotation using the interactive indication;
receiving a drawn object to be overlaid on the video segment during the desired time span; and
displaying the drawn object overlaid on the video segment when the desired time span is displayed.

8. The non-transitory computer-readable storage medium of claim 7, wherein receiving an indication of a desired time span comprises:
receiving a user indicated start time; and
automatically selecting an end time based on a default time span length.

9. The non-transitory computer-readable storage medium of claim 7, wherein receiving an annotation comprises:
receiving a user indicated title and a user indicated note; and
automatically inserting an author name into the annotation, wherein the author name corresponds to the user.

10. A non-transitory computer-readable storage medium including computer-readable instruction code for performing a method of recalling annotations based on a captured image, the method comprising:
receiving video from a telepresence device;
receiving an annotation from a first user corresponding to a frame in the video;
storing first location data corresponding to the frame;
storing the annotation;
receiving an image from a second device at a later time;
identifying second location data corresponding to the image;
retrieving the first location data and the annotation; and
displaying at least a portion of the annotation if the second location data is within a predetermined threshold of the first location data, wherein the first location data comprises at least one data element selected from the group consisting of a room number, a position of the telepresence device, an orientation of the telepresence device, a camera tilt, a camera pan, a camera zoom, and a set of image descriptors, and wherein the first location data corresponds to the frame in the video.

11. The non-transitory computer-readable storage medium of claim 10, wherein the first location data comprises general position information and a set of image descriptors.

12. The non-transitory computer-readable storage medium of claim 10, wherein receiving an annotation comprises receiving an annotation corresponding to an object in the frame, and wherein displaying comprises displaying at least the portion of the received annotation if a second set of image descriptors are within the predetermined threshold of a first set of image descriptors corresponding to the object.

13. The non-transitory computer-readable storage medium of claim 10, wherein the telepresence device comprises a robotic platform, wherein the first location data includes position and orientation data determined by a telepresence device component, and wherein inverse kinematics is used to compare the first location data to the second location data.

14. A non-transitory computer-readable storage medium including computer-readable instruction code for performing a method of spatially searching video, the method comprising:
receiving the video from a telepresence device;
storing the video;
receiving an indication of a spatial area of interest in a frame of the video from a user;
identifying one or more video segments from the stored video containing the spatial area of interest; and
providing indications of the one or more video segments to the user, wherein identifying one or more video segments comprises comparing the spatial area of interest to the stored video using an algorithm selected from the group consisting of a pattern-matching algorithm and an inverse kinematics algorithm.

15. The non-transitory computer-readable storage medium of claim 14, wherein identifying one or more video segments comprises determining whether a zoom level exceeds a predetermined threshold.

16. The non-transitory computer-readable storage medium of claim 14, wherein the method further comprises providing a rating for each of the one or more video segments to the user, wherein the rating is determined based on a size of the spatial area of interest in each of the one or more video segments.

17. A non-transitory computer-readable storage medium including computer-readable instruction code for performing a method of contextually searching video from a telepresence device, the method comprising:
receiving the video from the telepresence device;
storing the video;
storing situational data for each of a plurality of video segments;
receiving an indication of a situation of interest from a user;
identifying one or more matching video segments corresponding to the situation of interest; and
providing indications of the one or more matching video segments to the user, wherein the situational data comprises at least one data element selected from the group consisting of a patient name, a procedure being performed, and a remote practitioner operating the telepresence device.

18. The non-transitory computer-readable storage medium of claim 17, wherein the method further comprises:
   receiving a location-situation mapping from a local practitioner; and
   determining the situational data from location data.

19. The non-transitory computer-readable storage medium of claim 17, wherein receiving an indication of a situation of interest comprises receiving a filter criterion, and wherein providing indications comprises providing indications identifying each video segment according to a situational data element corresponding to the filter criterion.

20. A non-transitory computer-readable storage medium including computer-readable instruction code for performing a method of synchronized location and video replay, the method comprising:
   storing a plurality of video segments recorded by a telepresence device;
   storing corresponding location data for each of the plurality of video segments;
   navigating the telepresence device to a first location; and
   playing a first video segment corresponding to the first location while the telepresence device is at the first location, wherein the telepresence device is a mobile robot.

21. The non-transitory computer-readable storage medium of claim 20, wherein the method further comprises
   receiving a pause command from a user;
   pausing navigation and playback in response to the pause command; and
   providing control of the telepresence device to the user.

22. The non-transitory computer-readable storage medium of claim 20, wherein the method further comprises pausing playback of the first video segment if the telepresence device is more than a predetermined distance from the first location.

23. The non-transitory computer-readable storage medium of claim 20, wherein the method further comprises:
   storing text received from a user while at the first location; and
   associating the text in memory with the first video segment.

24. A non-transitory computer-readable storage medium including computer-readable instruction code for performing a method of monitoring visible trends, the method comprising:
   visiting a predetermined location with a telepresence device at predetermined time intervals;
   scanning the predetermined location for one or more predetermined areas of interest;
   recording video of each area of interest during each visit for a predetermined time period; and
   transmitting the recorded video to a storage device, wherein scanning the predetermined location comprises identifying an object of interest using at least one algorithm selected from the group consisting of scale-invariant feature transform (SIFT), speeded up robust features (SURF), and oriented features from accelerated segment test and rotated binary robust independent elementary features (ORB).

25. The non-transitory computer-readable storage medium of claim 24, wherein scanning the predetermined location comprises identifying a face using a Haarlike feature-matching algorithm.

26. The non-transitory computer-readable storage medium of claim 24, wherein the method further comprises transmitting a time stamp corresponding to the recorded video to the storage device.

27. A non-transitory computer-readable storage medium including computer-readable instruction code for performing a method of reorienting an object in a video, the method comprising:
   communicatively connecting a control device to a telepresence device;
   selectively displaying a video feed from the telepresence device in a video panel on an electronic display of the control device; receiving a zoom request associated with a selected portion of the video feed;
   magnifying the selected portion of the video feed;
   identifying informational content within the magnified selected portion of the video feed that is misaligned with respect to the orientation of the video feed; and
   digitally aligning the informational content with respect to the orientation of the video feed, wherein identifying informational content comprises identifying informational content selected from the group consisting of written or printed information on a document, information displayed on an electronic display, text, a chart, and an image.

28. The non-transitory computer-readable storage medium of claim 27, wherein magnifying the selected portion of the video feed comprises at least one of:
   transmitting instructions to adjust an optical zoom of a camera;
   digitally zooming the selected portion of the video feed; and
   transmitting navigation instructions to cause the telepresence device to navigate in the direction of the selected portion of the video feed.

29. The non-transitory computer-readable storage medium of claim 27, wherein digitally aligning the informational content with respect to the video feed comprises deskewing the informational content.

30. The non-transitory computer-readable storage medium of claim 27, wherein digitally aligning the informational content with respect to the video feed comprises rotating the informational content.

31. The non-transitory computer-readable storage medium of claim 27, wherein the operations further comprise:
   enhancing the informational content.

32. The non-transitory computer-readable storage medium of claim 31, wherein enhancing the informational content comprises adjusting a contrast of the informational content.

33. The non-transitory computer-readable storage medium of claim 31, wherein enhancing the informational content comprises synchronizing a refresh rate of the video feed based on a refresh rate of the informational content.

* * * * *

UNITED STATES PATENT AND TRADEMARK OFFICE
CERTIFICATE OF CORRECTION

PATENT NO. : 9,098,611 B2
APPLICATION NO. : 13/830334
DATED : August 4, 2015
INVENTOR(S) : Marco Pinter et al.

Page 1 of 1

It is certified that error appears in the above-identified patent and that said Letters Patent is hereby corrected as shown below:

In the Specification

At Column 1, Line 3, the following should be inserted:
--STATEMENT REGARDING FEDERALLY FUNDED RESEARCH OR DEVELOPMENT
This invention was made with government support under grant number R43 MD006709.--

Signed and Sealed this
Twenty-eighth Day of April, 2020

Andrei Iancu
*Director of the United States Patent and Trademark Office*